(12) United States Patent
Raichle et al.

(10) Patent No.: US 8,273,680 B2
(45) Date of Patent: Sep. 25, 2012

(54) PROCESS FOR PRODUCING GEOMETRIC SHAPED CATALYST BODIES

(75) Inventors: Andreas Raichle, Dresden (DE); Catharina Horstmann, Ludwigshafen (DE); Frank Rosowski, Mannheim (DE); Klaus Joachim Mueller-Engel, Stutensee (DE); Jochen Petzoldt, Weisenheim am Berg (DE); Ulrich Cremer, Mannheim (DE)

(73) Assignee: BASF SE, Ludwigshafen (DE)

( * ) Notice: Subject to any disclaimer, the term of this patent is extended or adjusted under 35 U.S.C. 154(b) by 179 days.

(21) Appl. No.: 12/557,021

(22) Filed: Sep. 10, 2009

(65) Prior Publication Data

US 2010/0069660 A1    Mar. 18, 2010

Related U.S. Application Data

(60) Provisional application No. 61/096,553, filed on Sep. 12, 2008.

(30) Foreign Application Priority Data

Sep. 12, 2008 (DE) .......................... 10 2008 042 061

(51) Int. Cl.
    *B01J 21/00*    (2006.01)
(52) U.S. Cl. ............ 502/243; 502/311; 502/8; 502/249
(58) Field of Classification Search .................. 502/243, 502/311, 8, 249
See application file for complete search history.

(56) References Cited

U.S. PATENT DOCUMENTS

| | | | |
|---|---|---|---|
| 6,383,976 B1 * | 5/2002 | Arnold et al. .................. | 502/311 |
| 7,122,707 B2 * | 10/2006 | Petzoldt et al. ................ | 568/479 |
| 7,129,195 B2 * | 10/2006 | Felder et al. ................... | 502/311 |
| 2005/0131253 A1 | 6/2005 | Teshigahara et al. | |
| 2008/0177105 A1 | 7/2008 | Raichle et al. | |

FOREIGN PATENT DOCUMENTS

| | | |
|---|---|---|
| DE | 24 35 860 A1 | 2/1976 |
| DE | 29 09 671 A1 | 10/1980 |
| DE | 33 38 380 A1 | 4/1984 |
| DE | 44 07 020 A1 | 9/1994 |
| DE | 44 42 346 A1 | 5/1996 |
| DE | 198 35 247 A1 | 2/1999 |
| DE | 199 10 506 A1 | 9/2000 |
| DE | 199 48 248 A1 | 4/2001 |
| DE | 199 48 523 A1 | 4/2001 |
| DE | 100 46 672 A1 | 3/2002 |
| DE | 100 46 957 A1 | 4/2002 |
| DE | 100 51 419 A1 | 4/2002 |
| DE | 101 22 027 A1 | 5/2002 |
| DE | 103 13 209 A1 | 3/2004 |
| DE | 102 45 585 A1 | 4/2004 |
| DE | 102 46 119 A1 | 4/2004 |
| DE | 103 13 208 A1 | 10/2004 |
| DE | 103 13 213 A1 | 10/2004 |
| DE | 103 37 788 A1 | 10/2004 |
| DE | 103 25 487 A1 | 12/2004 |
| DE | 10 2007 003778 | 1/2007 |
| DE | 10 2007 005 606 A1 | 4/2008 |
| DE | 10 2007 004 961 A1 | 7/2008 |
| DE | 10 2008 040093 | 7/2008 |
| DE | 10 2008 040 094 A1 | 1/2009 |
| DE | 10 2008 042 060 A1 | 6/2009 |
| EP | 0 000 835 A1 | 2/1979 |
| EP | 0 184 790 A2 | 6/1986 |
| EP | 0 468 290 A1 | 1/1992 |
| EP | 0 575 897 A1 | 12/1993 |
| EP | 0 700 714 A1 | 3/1996 |
| EP | 0 700 893 A1 | 3/1996 |
| EP | 0 990 636 A1 | 4/2000 |
| EP | 1 005 908 A2 | 6/2000 |
| EP | 1 106 598 A2 | 6/2001 |
| WO | WO 00/53557 A1 | 9/2000 |
| WO | WO 00/53558 A1 | 9/2000 |
| WO | WO 01/07431 A2 | 2/2001 |
| WO | WO 01/36364 A1 | 5/2001 |
| WO | WO 02/24620 A2 | 3/2002 |
| WO | WO 02/49757 A2 | 6/2002 |
| WO | WO 02/062737 A2 | 8/2002 |
| WO | WO 2005/030393 A1 | 4/2005 |
| WO | WO 2005030393 A1 * | 4/2005 |
| WO | WO 2005/042459 A1 | 5/2005 |
| WO | WO 2005/047224 A1 | 5/2005 |
| WO | WO 2005/049200 A1 | 6/2005 |
| WO | WO 2005/113127 A1 | 12/2005 |
| WO | WO 2007/082827 A1 | 7/2007 |

OTHER PUBLICATIONS

Dr. Helmut Brünner et al., "Hydrophobes „Aerosil" Herstellung, Eigenschaften and Verhalten, Chemiker-Zeitung Chemische Apparatur, vol. 89, Jul. 5, 1965, pp. 437-440.
U.S. Appl. No. 12/546,883, filed Aug. 25, 2009, Raichle, et al.
U.S. Appl. No. 12/494,991, filed Jun. 30. 2009, Eger, et al.
U.S. Appl. No. 61/077,638, filed Jul. 2, 2008, Raichle.

\* cited by examiner

*Primary Examiner* — Melvin C Mayes
*Assistant Examiner* — Melissa Stalder
(74) *Attorney, Agent, or Firm* — Oblon, Spivak, McClelland, Maier & Neustadt, L.L.P.

(57) ABSTRACT

A process for producing geometric shaped catalyst bodies K whose active material is a multielement oxide of stoichiometry $$[Bi_aZ^1{}_bO_x]_p[Bi_cMo_{12}Fe_dZ^2{}_eZ^3{}_fZ^4{}_gZ^5{}_hZ^6{}_iO_y]_1,$$

in which a finely divided oxide $Bi_aZ^1{}_bO_x$ and, formed from element sources, a finely divided mixture of stoichiometry $Bi_cMo_{12}Fe_dZ^2{}_eZ^3{}_fZ^4{}_gZ^5{}_hZ^6{}_i$ are mixed in a ratio of p:1, this mixture is used to form shaped bodies and these are treated thermally, where $0<c\leq 0.8$.

73 Claims, No Drawings

PROCESS FOR PRODUCING GEOMETRIC SHAPED CATALYST BODIES

The present invention relates to a process for producing geometric shaped catalyst bodies $K^S$ which comprise, as an active material, a multielement oxide $I^S$ of the general stoichiometry I $$[Bi_a Z^1_b O_x]_p [Mo_{12} Fe_d Z^2_e Z^3_f Z^4_g Z^5_h Z^6_i O_y]_1 \quad (I^S),$$

where
$Z^1$=tungsten or tungsten and molybdenum, with the proviso that at least 10 mol % of the molar total amount of $Z^1$ is tungsten,
$Z^2$=one element or more than one element from the group consisting of nickel and cobalt,
$Z^3$=one element or more than one element from the group consisting of the alkali metals, the alkaline earth metals and thallium,
$Z^4$=one element or more than one element from the group consisting of zinc, phosphorus, arsenic, boron, antimony, tin, cerium, vanadium, chromium and bismuth,
$Z^5$=one element or more than one element from the group consisting of silicon, aluminum, titanium, tungsten and zirconium,
$Z^6$=one element or more than one element from the group consisting of copper, silver and gold,
a=0.1 to 3,
b=0.1 to 10,
d=0.01 to 5,
e=1 to 10,
f=0.01 to 2,
g=0 to 5,
h=0 to 10,
i=0 to 1,
p=0.05 to 6, and
x, y=numbers determined by the valency and frequency of the elements in $I^S$ other than oxygen,
in which
a finely divided mixed oxide $Bi_a Z^1_b O_x$ with a particle diameter $d_{50}^{A1}$, as starting material A1, is preformed with the proviso that 1 µm≦$d_{50}^{A1}$≦100 µm;
sources of the elements other than oxygen in the component $T^S$=$[Mo_{12} Fe_d Z^2_e Z^3_f Z^4_g Z^5_h Z^6_i O_y]_1$ of the multielement oxide $I^S$ are used in an aqueous medium to obtain an intimate aqueous mixture M, with the proviso that
each of the sources used, in the course of preparation of the aqueous mixture M, passes through a degree of division Q for which its diameter $d_{90}^Q$ is ≦5 µm, and
the aqueous mixture M comprises the elements Mo, Fe, $Z^2$, $Z^3$, $Z^4$, $Z^5$ and $Z^6$ in the stoichiometry $I^{S*}$ $$Mo_{12} Fe_d Z^2_e Z^3_f Z^4_g Z^5_h Z^6_i \quad (I^{S*}),$$

the aqueous mixture M, by means of drying and adjusting the degree of division $d_{90}^{A2}$, is used to obtain a finely divided starting material A2 with a particle diameter $d_{90}^{A2}$, with the proviso that 400 µm≧$d_{90}^{A2}$≧10 µm;
starting material A1 and starting material A2, or starting material A1, starting material A2 and finely divided shaping assistant, are mixed with one another to form a finely divided starting material A3, with the proviso that the starting material A3 comprises the elements other than oxygen introduced into the starting material A3 via starting materials A1 and A2 in the multielement oxide $I^S$ in the stoichiometry $I^{S}$ $$[Bi_a Z^1_b]_p [Mo_{12} Fe_d Z^2_e Z^3_f Z^4_g Z^5_h Z^6_i]_1 \quad (I^{S}),$$

finely divided starting material A3 is used to form geometric shaped bodies V, and the shaped bodies V are treated thermally at elevated temperature to obtain the geometric shaped catalyst bodies $K^S$.

The present invention further relates to the use of shaped catalyst bodies $K^S$.

Geometric shaped catalyst bodies $K^{S*}$ which comprise a multielement oxide $I^S$ as an active material and processes for producing such shaped catalyst bodies are known (cf., for example, German application 102007003778.5, EP-A 575 897, WO 2007/017431, WO 02/24620, WO 2005/42459, WO 2005/47224, WO 2005/49200, WO 2005/113127, German application 102008040093.9, German application 102008040094.7 and DE-A 102007005606).

It is additionally known that catalysts $K^S$ (geometric shaped catalyst bodies $K^S$) are suitable for performing heterogeneously catalyzed partial oxidations of alkanes, alkanols, alkenes and/or alkenals having from 3 to 6 carbon atoms in the gas phase.

A full oxidation of an organic compound with molecular oxygen is understood in this document to mean that the organic compound is converted under the reactive action of molecular oxygen such that all carbon present in the organic compound is converted to oxides of carbon and all hydrogen present in the organic compound is converted to oxides of hydrogen. All different conversions of an organic compound under the reactive action of molecular oxygen are summarized in this document as partial oxidations of an organic compound.

In particular, partial oxidations shall be understood in this document to mean those conversions of organic compounds under the reactive action of molecular oxygen in which the organic compound to be oxidized partially, after the reaction has ended, comprises at least one oxygen atom more in chemically bound form than before performance of the partial oxidation.

In this document, the term "partial oxidation", however, shall also comprise oxidative dehydrogenation and partial ammoxidation, i.e. partial oxidation in the presence of ammonia.

Catalysts $K^S$ (geometric shaped catalyst bodies $K^S$) are particularly suitable for performing the heterogeneously catalyzed partial gas phase oxidation of propene to acrolein and of isobutene to methacrolein, and for performing the heterogeneously catalyzed partial gas phase ammoxidation of propene to acrylonitrile and of isobutene to methacrylonitrile.

In general, the heterogeneously catalyzed partial gas phase oxidation of propene (isobutene) to acrolein (methacrolein) forms the first stage of a two-stage heterogeneously catalyzed partial gas phase oxidation of propene (isobutene) to acrylic acid (methacrylic acid), as described by way of example in WO 2005/42459.

By-product formation of acrylic acid (methacrylic acid) which accompanies a heterogeneously catalyzed partial gas phase oxidation of propene (isobutene) to acrolein (methacrolein) is therefore generally not undesired and is normally included with the desired product of value formation.

It is additionally known that the performance (activity and selectivity of target product formation (product of value formation)) of geometric shaped catalyst bodies $K^S$, in the course of continuous operation of a heterogeneously catalyzed partial gas phase oxidation of alkanes, alkanols, alkenes and/or alkenals having from 3 to 6 carbon atoms (for example to the corresponding olefinically unsaturated aldehydes and/or carboxylic acids), initially increases with increasing operating time up to a maximum value (this applies in particular to the case of a partial gas phase oxidation of propene to acrolein and/or acrylic acid and of isobutene to methacrolein and/or methacrylic acid heterogeneously catalyzed by geometric shaped catalyst bodies $K^S$; however, it is also true for the case of a heterogeneously catalyzed partial gas phase ammoxidation of propene to acrylonitrile and of isobutene to methacrylonitrile). This operating phase with an increasing performance of the geometric shaped catalyst bodies $K^S$ is also referred to as the forming phase (or else, for short, simply as "forming") of the geometric shaped catalyst bodies $K^S$. It generally extends over periods of several months and in some cases even over more than one year, in the course of which activity and selectivity of target product formation reach their maximum value generally at different operating times.

One measure of the activity of geometric shaped catalyst bodies $K^S$ or of a catalyst bed comprising them is that temperature which is required to achieve a particular conversion of the organic compound (for example of the propene or of the isobutene) as the reaction gas mixture comprising the organic compound to be oxidized partially passes through the catalyst bed. When the catalyst bed is present, for example, in the tubes of a tube bundle reactor around which a salt bath flows, the inlet temperature of the salt bath which is required to achieve the desired partial oxidation conversion based on single pass of the reaction gas mixture through the catalyst bed into the tube bundle reactor can normally be lowered gradually, under otherwise unchanged operating conditions, with increasing activation of the catalyst bed. The operation of the catalyst bed at a lower temperature normally prolongs its lifetime.

The target product selectivity (product of value selectivity) is understood to mean the ratio of molar amount of product of value formed in single pass of the reaction gas mixture through the catalyst bed to converted molar amount of organic starting compound to be oxidized partially (·100 in mol %). In other words, an increased starting selectivity of product of value formation reduces the amount of raw material required for the preparation of a particular amount of product of value.

Overall, there is thus a general interest in geometric shaped catalyst bodies $K^S$ which, in the course of continuous operation of the heterogeneously catalyzed partial gas phase oxidation, have on the one hand a maximum starting activity and on the other hand ensure a maximum starting selectivity of product of value formation at the same time.

Characteristic features of the geometric shaped catalyst bodies $K^S$ recommended in the prior art are that they either exclude presence of the element Bi in the component $T^S$ of the multielement oxide I active material (cf., for example, EP-A 575 897, WO 02/04620) or at best include it as optional under "also rans" (cf., for example, DE-A 10 2007 004 961, WO 2007/017431 and German application 102008040093.9). The experimental working examples of the prior art exclude Bi in all cases as a constituent of the $T^S$ component of the particular multielement oxide $I^S$ active material.

In view of these facts, it was an object of the present invention to provide geometric shaped bodies $K^S$ and a process for preparing them, which, especially in the context of use for a heterogeneously catalyzed gas phase oxidation of propene to acrolein and of isobutene to methacrolein, in the course of continuous operation of partial oxidation, both ensure an increased starting selectivity of product of value formation and have an increased starting activity, as far as possible without any significant reduction in their long term stability.

This object is achieved by virtue of provision of a process for producing geometric shaped catalyst bodies K which comprise, as an active material, a multielement oxide I of the general stoichiometry I

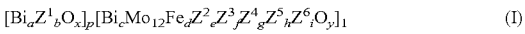

where
$Z^1$=tungsten or tungsten and molybdenum, with the proviso that at least 10 mol % of the molar total amount of $Z^1$ is tungsten,
$Z^2$=one element or more than one element from the group consisting of nickel and cobalt,
$Z^3$=one element or more than one element from the group consisting of the alkali metals, the alkaline earth metals and thallium,
$Z^4$=one element or more than one element from the group consisting of zinc, phosphorus, arsenic, boron, antimony, tin, cerium, vanadium and chromium,
$Z^5$=one element or more than one element from the group consisting of silicon, aluminum, titanium, tungsten and zirconium,
$Z^6$=one element or more than one element from the group consisting of copper, silver, gold, yttrium, lanthanum and the lanthanides,
a=0.1 to 3,
b=0.1 to 10,
d=0.01 to 5,
e=1 to 10,
f=0.01 to 2,
g=0 to 5,
h=0 to 10,
i=0 to 1,
p=0.05 to 6, and
x, y=numbers determined by the valency and frequency of the elements in I other than oxygen,
in which
a finely divided mixed oxide $Bi_aZ^1{}_bO_x$ with a particle diameter $d_{50}{}^{A1}$, as starting material A1, is preformed with the proviso that 1 μm≦$d_{50}{}^{A1}$≦100 μm;
sources of the elements other than oxygen in the component T=[$Bi_cMo_{12}Fe_dZ^2{}_eZ^3{}_fZ^4{}_gZ^5{}_hZ^6{}_iO_y$]$_1$ of the multielement oxide I are used in an aqueous medium to obtain an intimate aqueous mixture M, with the proviso that
  each of the sources used, in the course of preparation of the aqueous mixture M, passes through a degree of division Q for which its diameter $d_{90}{}^Q$ is ≦5 μm,
and
the aqueous mixture M comprises the elements Bi, Mo, Fe, $Z^2$, $Z^3$, $Z^4$, $Z^5$ and $Z^6$ in the stoichiometry I*

the aqueous mixture M, by means of drying and adjusting the degree of division $d_{90}{}^{A2}$, is used to obtain a finely divided starting material A2 with a particle diameter $d_{90}{}^{A2}$, with the proviso that 400 μm≧$d_{90}{}^{A2}$≧10 μm;
starting material A1 and starting material A2, or starting material A1, starting material A2 and finely divided shaping assistant, are mixed with one another to form a finely divided starting material A3, with the proviso that the starting material A3 comprises the elements other than oxygen introduced into the starting material A3 via starting materials A1 and A2 in the multielement oxide I in the stoichiometry I**

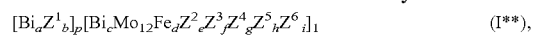

finely divided starting material A3 is used to form geometric shaped bodies V, and
the shaped bodies V are treated thermally at elevated temperature to obtain the geometric shaped catalyst bodies K, wherein the stoichiometric coefficient c satisfies the condition 0<c≦0.8.

According to the invention, c is preferably $\geq 0.001$, advantageously $\geq 0.002$ and, more preferably, c is $\geq 0.003$ or $\geq 0.005$.

Taking account of the aspect of the long-term stability of the inventive geometric shaped catalyst bodies K (especially in the context of a heterogeneously catalyzed partial gas phase oxidation of propene to acrolein or of isobutene to methacrolein), c is appropriately in application terms $\leq 0.7$ or $\leq 0.6$.

Values of c which are particularly favorable in accordance with the invention thus satisfy, for example the relationships $0.007 \leq c \leq 0.5$, or $0.01 \leq c \leq 0.4$, or $0.02 \leq c \leq 0.3$, or $0.03 \leq c \leq 0.2$, or $0.04 \leq c \leq 0.1$. A further range of values which is advantageous in accordance with the invention is the range of $0.005 \leq c \leq 0.08$, or $0.01 \leq c \leq 0.06$.

In addition, it is advantageous in accordance with the invention when p is 0.1 to 4, or 0.2 to 3, or 0.2 to 2, or 0.3 to 1.

Moreover, it is advantageous for the inventive objectives when the ratio of the total molar amount of Bi present in the multielement oxide I ($n_{Bi}$) to the total molar amount of Mo present in the multielement oxide I ($n_{Mo}$), i.e. $n_{Bi}:n_{Mo}$, is (0.3 to 2):12, preferably (0.4 to 1.8):12, and more preferably (0.5 to 1.6):12.

In addition, it is favorable for the inventive procedure when $1~\mu m \leq d_{50}^{A1} \leq 75~\mu m$, or $1~\mu m \leq d_{50}^{A1} \leq 50~\mu m$, or $1~\mu m \leq d_{50}^{A1} \leq 25~\mu m$. Further preferred ranges of values for $d_{50}^{A1}$ are the ranges of $1~\mu m \leq d_{50}^{A1} \leq 10~\mu m$, $1.2~\mu m \leq d_{50}^{A1} \leq 8~\mu m$, $1.5~\mu m \leq d_{50}^{A1} \leq 6~\mu m$, $1.5~\mu m \leq d_{50}^{A1} \leq 4~\mu m$ and $2~\mu m \leq d_{50}^{A1} \leq 3~\mu m$.

In a corresponding manner, it is advantageous in accordance with the invention when $300~\mu m \geq d_{90}^{A2} \geq 10~\mu m$, or $200~\mu m \geq d_{90}^{A2} \geq 20~\mu m$, or $170~\mu m \geq d_{90}^{A2} \geq 30~\mu m$, or $150~\mu m \geq d_{90}^{A2} \geq 40~\mu m$, or $130~\mu m \geq d_{90}^{A2} \geq 40~\mu m$. Also favorable is $100~\mu m \geq d_{90}^{A2} \geq 50~\mu m$.

It is also found to be advantageous for the process according to the invention when, for the finely divided starting material A2, also, $10~\mu m \leq d_{50}^{A2} \leq 100~\mu m$, preferably $20~\mu m \leq d_{50}^{A2} \leq 60~\mu m$.

Finally, it is additionally advantageous for the process according to the invention when the ratio of the particle diameter $d_{90}^{A2}$ of the finely divided starting material A2 to the particle diameter $d_{10}^{A2}$ of the finely divided starting material A2, i.e. a $d_{90}^{A2}:d_{10}^{A2}$ (reported in the same length unit) is in the range from 5 to 20, preferably in the range from 10 to 15.

To determine particle diameter distributions in dry powders and the particle diameters which can be obtained therefrom, for example $d_{10}$, $d_{50}$ and $d_{90}$, the particular finely divided powder (unless explicitly stated otherwise) was conducted through a dispersing channel into the Sympatec RODOS dry disperser (Sympatec GmbH, System-Partikel-Technik, Am Pulverhaus 1, D-38678 Clausthal-Zellerfeld), dry-dispersed there with compressed air and blown into the test cell in a free jet. In this test cell, the volume-based particle diameter distribution is then determined to ISO 13320 with the Malvern Mastersizer S laser diffraction spectrometer (Malvern Instruments, Worcestershire WR14 1AT, United Kingdom). The particle diameters $d_x$ reported as the measurement results are defined such that X % of the total particle volume consists of particles having this or a smaller diameter. This means that (100–X) % of the total particle volume consists of particles with a diameter $>d_x$. Unless explicitly stated otherwise in this document, particle diameter determinations and $d_x$ values obtained therefrom, for example $d_{90}^{Q}$, $d_{50}^{A1}$ and $d_{90}^{A2}$, are based on a dispersion pressure employed in the determination (which determines the degree of dispersion of the dry powder during the measurement) of 2 bar absolute.

All data relating to an X-ray diffractogram in this document is based on an X-ray diffractogram obtained using Cu-K$\alpha$ radiation as the X-radiation (Theta-Theta Bruker D8 Advance diffractometer, tube voltage, 40 kV, tube current: 40 mA, V20 aperture (variable), V20 collimator (variable), detector aperture (0.1 mm), measurement interval (2$\Theta$=2 theta): 0.02°, measurement time per step: 2.4 s, detector: Si semiconductor detector).

The definition of the intensity of a reflection in the X-ray diffractogram is based in this document on the definition laid down in DE-A 198 35 247, and that laid down in DE-A 100 51 419 and DE-A 100 46 672.

In other words, when $A^1$ denotes the peak location of a reflection 1 and when $B^1$ denotes the closest pronounced minimum in the line of the X-ray diffractogram when viewed along the intensity axis at right angles to the 2$\Theta$ axis (neglecting minima displaying reflection shoulders) to the left of the peak location $A^1$, and when $B^2$ correspondingly denotes the closest pronounced minimum to the right of the peak location $A^1$, and $C^1$ denotes the point at which a straight line drawn from the peak location $A^1$ at right angles to the 2$\Theta$ axis intersects with a straight line connecting points $B^1$ and $B^2$, the intensity of the reflection 1 is the length of the straight line section $A^1C^1$ which extends from the peak location $A^1$ to the point $C^1$. The expression "minimum" means a point at which the gradient of slope of a tangent applied to the curve in a base region of the reflection 1 goes from a negative value to a positive value, or a point at which the gradient of slope tends to zero, employing the coordinates of the 2$\Theta$ axis and of the intensity axis to determine the gradient of slope. An illustrative performance of an intensity determination is shown by FIG. 6 in DE-A 100 46 672. Detailed remarks regarding intensity determination of X-ray diffraction reflections can also be found in DE-A 101 22 027. Statements regarding half-height widths of diffraction lines are based in this document, correspondingly, on the length of the straight line section which arises between the two points of intersection $H^1$ and $H^2$ when a parallel to the 2$\Theta$ axis is drawn in the middle of the straight line section $A^1C^1$, where $H^1$, $H^2$ mean the first point of intersection in each case of this parallel line with the line in the X-ray diffractogram as defined above to the left and to the right of $A^1$. In general, the half-height widths of X-ray diffraction reflections of the multielement oxide I active materials are $\leq 1°$, and usually $\leq 0.5°$.

All figures in this document for specific surface areas of solids are based on determinations to DIN 66131 (determination of the specific surface area of solids by gas adsorption ($N_2$) according to Brunauer-Emmet-Teller (BET)), unless explicitly stated otherwise.

The inventive requirement that each source of the elements other than oxygen in the components $T=[Bi_cMo_{12}Fe_dZ^2_eZ^3_fZ^4_gZ^5_hZ^6_iO_y]_1$ of the multielement oxide I, in the course of preparation of the aqueous mixture M, must pass through a degree of division Q whose diameter $d_{90}^{Q}$ is $\leq 5~\mu m$ expresses that it is quite possible to proceed from a coarser-grain source (from a coarser-grain starting material). However, on the route of incorporation of such a source into the aqueous mixture M, this source must at least once meet the requirement $d_{90}^{Q} \leq 5~\mu m$ (of course, $d_{90}^{Q}$ is always $>0~\mu m$).

In principle, the condition $d_{90}^{Q} \leq 5~\mu m$ is met when a source is dissolved in a solvent (for example in an aqueous medium; the term "dissolution" is meant here in the sense of molecular or ionic dissolution), and the resulting solution is used to prepare the aqueous mixture M.

This is caused by the fact that, when a source (starting compound, starting substance) is dissolved in a solvent, the source is distributed molecularly or ionically in the solvent.

This means that the largest geometric unit of the dissolved starting substance (source) present in the solution unavoidably has "molecular" dimensions which are thus necessarily significantly smaller than 5 µm. It will be appreciated that it is also possible for more than one source (where one source may also comprise more than one element of the component T and hence simultaneously be the source of more than one element) of an element of the component T to be dissolved in one and the same solution, and for the resulting solution to be used to prepare the aqueous mixture M.

However, the requirement $d_{90}^Q \leq 5$ µm is also met when a source of an element of the component T is present in a solvent in a colloidal solution.

Colloidal solutions constitute a connection between true (molecular or ionic) solutions and suspensions. In these colloidally dispersed systems there are relatively small accumulations of molecules or atoms which, however, are detectable neither with the naked eye nor with a microscope.

The colloidal solution appears visually to be entirely clear (though it is often colored), since the particles present therein have only a diameter of from 1 to 250 nm (preferably to 150 nm and more preferably to 100 nm), and the corresponding $d_{90}^Q$ is therefore necessarily $\leq 5$ µm. Owing to the small size, a removal of the colloidally dissolved particles by conventional filtration is not possible. They can, however, be separated from their "solvent" by ultrafiltration with membranes of vegetable, animal or synthetic origin (for example parchment, pig's bladder or cellophane). In contrast to the "visually empty" true (molecular or ionic) solutions, a light beam cannot pass through a colloidal solution without being deflected. The light beam is scattered and deflected by the colloidally dissolved particles. In order to keep colloidal solutions stable and to prevent further particle agglomerations, they frequently comprise added wetting and dispersing assistants and other additives.

For example, the element silicon in the process according to the invention can be introduced in the form of a silica sol to prepare the aqueous mixture M. Silica sols are colloidal solutions of amorphous silicon dioxide in water. They are as mobile as water and do not comprise any sedimentable constituents. Their $SiO_2$ content may be up to 50% by weight and more with a shelf life often of several years (without sedimentation).

However, the requirement $d_{90}^Q \leq 5$ µm is also met when a source is, for example, dry-comminuted (for example by grinding) to this particle size.

In principle, such a powder can be used directly as such to prepare the intimate aqueous mixture M. Of course, it can also be suspended in a liquid medium and then used in the form of this suspension to prepare the aqueous mixture M.

Preferably in accordance with the invention, $d_{90}^Q$ for all sources used to prepare the aqueous mixture M (starting compounds, starting substances) is $\leq 4$ µm or $\leq 3$ µm, more preferably $\leq 2$ µm or $\leq 1$ µm and most preferably $\leq 0.8$ µm or $\leq 0.5$ µm. Even better, $d_{90}^Q$ for all sources used to prepare the aqueous mixture M (starting compounds, starting substances) is $\leq 0.3$ µm or $\leq 0.2$ µm.

Particular preference is given to those processes according to the invention in which, in the course of preparation of the aqueous mixture M, all sources used of the elements of the component T pass through the state of a colloidal solution or of a true (molecular or ionic) solution (the resulting aqueous mixtures M shall be referred to in this document as aqueous mixtures $M^L$).

Very particular preference is given to those processes according to the invention in which, in the course of preparation of the aqueous mixture M, all sources used of the elements other than silicon in the component T pass through the state of a true (molecular or ionic) solution (the resulting aqueous mixtures M shall be referred to in this document as aqueous mixture $M^{L*}$). When the aqueous mixture M further comprises a source of the element silicon, it is advantageously a colloidal solution thereof (more preferably a silica sol). Such aqueous mixtures M shall be referred to in this document as aqueous mixtures $M^{L**}$.

An intimate aqueous mixture M shall be understood in this document to mean those mixtures M whose component which escapes in gaseous form on conversion from the aqueous mixture M to the finely divided starting material A2 consists of water vapor to an extent of at least 50% of its weight, advantageously to an extent of at least 60% of its weight, particularly advantageously to an extent of at least 70% of its weight, very particularly advantageously to an extent of 80% of its weight and even better to an extent of 90% of its weight. As well as water, the aforementioned component which escapes in gaseous form may also comprise compounds such as HCl, $HNO_3$, carbon dioxide, ammonia, alcohols (e.g. methanol, ethanol, glycol and glycerol), ketones, for example acetone or other organic compounds which are soluble in water under standard conditions (1 atm, 25° C.).

Useful sources of the elements of the component T of the desired inventive multielement oxide active material I are in principle those compounds which are already oxides and/or those compounds which are convertible to oxides by heating, at least in the presence of molecular oxygen.

As well as the oxides, useful such starting compounds (sources) may in particular be halides, nitrates, formates, oxalates, citrates, acetates, carbonates, amine complexes, ammonium salts and/or hydroxides (and the hydrates of the aforementioned salts).

A favorable Mo source is ammonium heptamolybdate tetrahydrate. However, it is also possible in principle to use molybdenum trioxide, for example. $Z^2$ sources favorable in accordance with the invention are the nitrates and nitrate hydrates of the $Z^2$ elements. $Z^3$ sources advantageous in accordance with the invention are the hydroxides and nitrates of the $Z^3$ elements and hydrates thereof. For the element iron, an iron nitrate hydrate is advantageously used in the process according to the invention. The bismuth sources used for the preparation of the aqueous mixture M will preferably be water-soluble salts of bismuth such as nitrates, carbonates, hydroxides and/or acetates, or directly the aqueous solutions thereof.

Silica sol constitutes the Si source preferred in accordance with the invention. Lanthanides preferred in accordance with the invention are Er, Tb, Ho, Eu, Tm, Nd, Lu, Dy, Gd, Ce and Sm. The sources thereof used are preferably, just as in the case of La and Y, the corresponding nitrate hydrates.

In addition to the relevant sources of the elements of component T of the multielement oxide I, it is also possible for substances which decompose and/or are destroyed (converted chemically) to form compounds which escape in gaseous form at least under the conditions of the thermal treatment of the geometric shaped bodies V to form the geometric shaped catalyst bodies K to be incorporated into the particular aqueous mixture M. Substances of this kind may, for example, function as pore formers and be included for the purpose of adjusting the active internal surface area. Useful such (auxiliary) substances include, for example, $NH_4OH$, $(NH_4)_2CO_3$, $NH_4HCO_3$, $NH_4NO_3$, urea, $NH_4CHO_2$, $H_2CO_3$, $HNO_3$, $H_2SO_4$, $NH_4CH_3CO_2$, $NH_4Cl$, HCl, $NH_4HSO_4$, $(NH_4)_2SO_4$, ammonium oxalate, hydrates of the aforementioned compounds and organic substances, for example stearic acid, malonic acid, ammonium salts of the aforementioned acids, starches (e.g. potato starch and corn starch), cellulose, ground nutshells, finely ground polymer (e.g. polyethylene, polypropylene), etc.

Preferably in accordance with the invention, the finely divided starting material A2 is obtained from the aqueous mixture M (especially in the case of an aqueous mixture $M^L$, or $M^{L*}$, or $M^{L**}$) by spray-drying thereof. This means that the aqueous mixture M in this case is first divided into fine droplets and these are then dried. Preference is given in accordance with the invention to effecting the drying in a hot air stream. In principle, the aforementioned spray drying can also be accomplished using other hot gases (e.g. nitrogen, or nitrogen-diluted air or else other inert gases).

The spray drying can in principle be effected either in cocurrent or in countercurrent flow of the droplets to the hot gas. It is preferably effected in countercurrent flow of the droplets to the hot gas, more preferably in hot air countercurrent flow. Typical gas inlet temperatures are in the range from 250 to 450° C., preferably from 270 to 370° C. Typical gas outlet temperatures are in the range from 100 to 160° C.

Preferably in accordance with the invention, the spray drying is carried out in such a way as to directly give rise to the particle diameter $d_{90}^{A2}$ desired for the finely divided starting material A2 as a result of the spray drying (i.e. is the corresponding $d_{90}$ of the resulting spray powder), such that the resulting spray powder can directly constitute the starting material A2 for use in accordance with the invention.

When the degree of division of the resulting spray powder is too small compared to the desired $d_{90}^{A2}$, it can be coarsened in a controlled manner, for example by subsequent compaction, to The degree of division desired for the starting material A2. Conversely, the fineness of the spray powder resulting directly in the spray drying can also be increased if required by grinding to the degree of division desired for the starting material A2.

It will be appreciated that the intimate aqueous mixture M can also first be dried by conventional evaporation (preferably under reduced pressure; the drying temperature generally should not exceed 150° C.), and the resulting dry material can be adjusted by subsequent comminution to the degree of division $d_{90}^{A2}$ required in accordance with the invention. In principle, the aqueous mixture M can also be dried in the process according to the invention by freeze drying.

$Z^2$ in the process according to the invention is preferably exclusively Co.

$Z^3$ in the process according to the invention is preferably K, Cs and/or Sr, more preferably K.

$Z^5$ in the process according to the invention is preferably Si.

The stoichiometric coefficient a is advantageously from 0.3 to 3, preferably from 0.5 to 3 and more preferably from 1.5 to 2.5.

The stoichiometric coefficient b is advantageously from 1 to 6, particularly advantageously from 2 to 5 and very particularly advantageously from 3 to 5.

Preferably in accordance with the invention, at least 20 mol %, better at least 40 mol % or at least 50 mol %, and even better at least 60 mol % or at least 80 mol %, and at best at least 90 mol % or 100 mol %, of the molar total amount of $Z^1$ is tungsten.

The stoichiometric coefficient e is preferably from 3 to 8, particularly advantageously from 4 to 7 and very particularly advantageously from 5 to 6.

The stoichiometric coefficient f is advantageously from 0.02 to 2 and particularly advantageously from 0.03 to 1 or from 0.05 to 0.5.

The stoichiometric coefficient d is advantageously from 0.1 to 4.5, preferably from 0.5 to 4 and more preferably from 1 to 4 or from 2 to 4.

The stoichiometric coefficient h is preferably from >0 to 10, more preferably from 0.1 to 8 or from 0.2 to 7, even more preferably from 0.3 to 6 or from 0.4 to 5, and most advantageously from 0.5 to 3 or from 1 to 3.

The stoichiometric coefficients g and i may both simultaneously be 0, but may also independently assume values other than 0.

This means that the working examples B1 to B13 and the comparative examples V1 to V15 (these thus become examples) can also be carried out under otherwise unchanged conditions (including the subsequent use as catalysts for propene partial oxidation) using finely divided starting material A2 whose corresponding stoichiometry I* is
$Mo_{12}Ni_{3.0}CO_{2.5}Fe_{3.0}Bi_{0.01}Si_{1.6}K_{0.08}$, or
$Mo_{12}Ni_{3.0}Co_4Fe_{3.0}Bi_{0.02}Si_{1.6}K_{0.08}$, or
$Mo_{12}Sb_{0.2}Co_{4.2}Fe_{1.4}Zn_{0.2}Bi_{0.03}W_{0.1}K_{0.06}$, or
$Mo_{12}Sb_{0.2}Co_{4.2}Fe_{1.4}Zn_{0.2}Bi_{0.8}W_{0.1}K_{0.06}$, or
$Mo_{12}Ni_{2.8}Co_{5.2}Fe_{1.8}Bi_{0.05}K_{0.1}$, or
$Mo_{12}Ni_{2.8}Co_{5.2}Fe_{1.8}Bi_{0.7}K_{0.1}$, or
$Mo_{12}Co_5Fe_1Ni_3W_{0.5}Bi_{0.1}K_{0.1}$, or
$Mo_{12}Co_5Fe_1Ni_3W_{0.5}Bi_{0.8}K_{0.1}$, or
$Mo_{12}Co_7Fe_{3.0}Bi_{0.02}Si_{1.6}K_{0.08}$, or
$Mo_{12}Co_7Fe_{3.0}Bi_{0.05}Si_{1.6}K_{0.08}$, or
$Mo_{12}Co_7Fe_{3.0}Bi_{0.1}Si_{1.6}K_{0.08}$, or
$Mo_{12}Co_7Fe_{3.0}Bi_{0.2}Si_{1.6}K_{0.08}$, or
$Mo_{12}Co_7Fe_{3.0}Bi_{0.5}Si_{1.6}K_{0.08}$, or
$Mo_{12}Co_7Fe_{3.0}Bi_{0.01}Si_{1.6}K_{0.08}$, or
$Mo_{12}Co_{5.5}Fe_{3.0}Bi_{0.02}Gd_{0.05}Si_{1.6}K_{0.08}$, or
$Mo_{12}Co_{5.5}Fe_{3.0}Bi_{0.03}Y_{0.05}Si_{1.6}K_{0.08}$, or
$Mo_{12}Co_{5.5}Fe_{3.0}Bi_{0.01}Er_{0.05}Si_{1.6}K_{0.08}$, or
$Mo_{12}Co_{5.5}Fe_{3.0}Bi_{0.02}Sm_{0.05}Si_{1.6}K_{0.08}$, or
$Mo_{12}Co_{5.5}Fe_{3.0}Bi_{0.06}Eu_{0.05}Si_{1.6}K_{0.08}$, or
$Mo_{12}Co_{5.5}Fe_{3.0}Bi_{0.03}Dy_{0.05}Si_{1.6}K_{0.08}$, or
$Mo_{12}Co_{5.5}Fe_{3.0}Bi_{0.02}Yb_{0.05}Si_{1.6}K_{0.08}$, or
$Mo_{12}Co_{5.5}Fe_{3.0}Bi_{0.03}Tb_{0.05}Si_{1.6}K_{0.08}$, or
$Mo_{12}Co_{5.5}Fe_{3.0}Bi_{0.05}Ho_{0.05}Si_{1.6}K_{0.08}$, or
$Mo_{12}Co_{5.5}Fe_{3.0}Bi_{0.04}Ce_{0.05}Si_{1.6}K_{0.08}$, or
$Mo_{12}Co_{5.5}Fe_{3.0}Bi_{0.06}La_{0.05}Si_{1.61}K_{0.08}$. Elements which are not present in the finely divided starting material A2 of example B1 but are comprised by the above stoichiometries are dissolved in the solution B using nitrate hydrates thereof as the source. In a departure from this, W is added to the solution A as ammonium paratungstate.

At the same time, in all aforementioned configurations, and in working examples B1 to B13, $d_{50}^{A1}$ may also be 2.2 μm, or 2.4 μm, or 2.6 μm, or 2.8 μm, or 3.0 μm, or 3.5 μm, or 4.0 μm, or 4.5 μm, or 5.0 μm, or 5.5 μm, or 6.0 μm, or 6.5 μm, or 7.0 μm.

Moreover, in all aforementioned cases, including all working examples B1 to B13, $d_{90}^{A2}$ may also be 50 μm, or 52 μm, or 54 μm, or 56 μm, or 58 μm, or 60 μm, or 62 μm, or 64 μm, or 66 μm, or 68 μm, or 70 μm, or 72 μm, or 74 μm, or 76 μm, or 78 μm, or 80 μm, or 82 μm, or 84 μm, or 86 μm, or 88 μm or 90 μm. By way of example, in all aforementioned cases, $d_{50}^{A1}=2.4$ μm and $d_{90}^{A2}=68$ μm. The stoichiometric coefficient p may also be 0.25, or 0.35, or 0.4.

The finely divided mixed oxide $Bi_aZ^1{}_b$ can be preformed in a manner known per se (cf., for example, EP-A 575 897, DE-A 3338380, EP-A 835, WO 02/24620, WO 2007/017431, German application 102007003778.5, WO 2005/030393 and German application 102008040093.9).

In general, at least one source of the element Bi and at least one source of the element W and if appropriate a source of the element Mo (i.e. at least one starting compound comprising the element Bi and at least one starting compound comprising the element W and if appropriate a starting compound comprising the element Mo) will be mixed intimately with one another in aqueous medium, the aqueous mixture will be dried and the resulting dry material will be calcined (treated thermally) at temperatures in the range from 400 to 900° C. (preferably from 600 to 900° C. and more preferably from 700 to 900° C.), and the particle diameter $d_{50}^{A1}$ required in accordance with the invention will be established by comminuting the resulting calcination products to obtain the finely divided starting material A1. Useful sources of the Bi, W and Mo are in principle those compounds which are already oxides of these elements, or those compounds which are convertible to oxides by heating, at least in the presence of molecular oxygen.

Preferably, water-soluble salts of bismuth such as nitrates, carbonates, hydroxides and/or acetates, with tungstic acid (the essentially water-insoluble tungstic acid is preferably used in the form of fine powder whose $d_{90}$ is appropriately in application terms $\leq 5$ μm or $\leq 2$ μm, preferably from 0.1 to 1 μm) and/or ammonium salts thereof will be mixed into water, the aqueous mixture will be dried (preferably spray-dried), and the dried material will subsequently be treated thermally as described. If Mo is also used, the Mo source used may be, for example, molybdenum trioxide or ammonium heptamolybdate tetrahydrate.

When the drying has been effected by spray drying, the resulting spray powder will advantageously be coarsened before the calcination (for example, advantageously in application terms, will be pasted with addition of up to 20% by weight of water and, for example, extruded by means of an extruder to give extrudates which are easy to handle for calcination purposes; these are subsequently dried and then calcined). Typically, the thermal treatment is effected in an airstream (for example, in the case of the aforementioned extrudates, in a rotary tube oven as described in DE-A 103 25 487). The division of the resulting calcined mixed oxide to the particle diameter $d_{50}^{A1}$ which is essential in accordance with the invention will normally be brought about by grinding in mills. If required, the millbase is subsequently classified to the desired degree of comminution.

Preferred mixed oxides $Bi_a Z^1_b$ formed beforehand in the process according to the invention are the mixed oxides $Bi_2W_4O_{15}$ ($Bi_2W_2O_9.2\ WO_3$), $Bi_2W_2O_9$, $Bi_2W_{2.5}O_{10.5}$ ($Bi_2W_2O_9.\frac{1}{2}WO_3$), $Bi_2W_3O_{12}$($Bi_2W_2O_9.WO_3$), $Bi_2W_5O_{18}$ ($Bi_2W_2O_9.3WO_3$), $Bi_2W_6O_{21}$ ($Bi_2W_2O_9.4\ WO_3$), $Bi_2W_8O_{27}$ ($Bi_2W_2O_9.6\ WO_3$) and $Bi_2W_1O_6$, among which $Bi_2W_4O_{15}$ is very particularly preferred in accordance with the invention (working examples B1 to B13 and comparative examples V1 to V15 (including the use thereof for propene partial oxidation) can therefore also be implemented using $Bi_2W_3O_{12}$, or $Bi_2W_5O_{18}$, or $Bi_2W_6O_{21}$, or $Bi_2W_8O_{27}$, or $Bi_2W_1O_6$, or $Bi_2W_2O_9$ as the finely divided starting material A1 of particle size corresponding to the finely divided $Bi_2W_4O_{15}$ used).

In the same way as they are incorporated into the aqueous mixture M, it is also possible to additionally incorporate, into the aqueous mixture of the at least one Bi source and of the at least one W source (and if appropriate additional Mo source), in the course of preparation of the mixed oxide $Bi_a Z^1_b O_x$, substances which, under the conditions of the thermal treatment employed to form the mixed oxide $Bi_a Z^1_b O_x$, decompose and/or are destroyed (converted chemically) to give compounds which escape in gaseous form. Such substances may, for example, function as pore formers and be included for the purpose of influencing the active internal surface area of the mixed oxide $Bi_a Z^1_b O_x$.

Useful (auxiliary) substances of this kind include, for example, $NH_4OH$, $(NH_4)_2CO_3$, $NH_4HCO_3$, $NH_4NO_3$, urea, $NH_4CHO_2$, $H_2CO_3$, $HNO_3$, $H_2SO_4$, $NH_4CH_3CO_2$, $NH_4HSO_4$, $NH_4Cl$, $HCl$, $(NH_4)_2SO_4$, ammonium oxalate, hydrates of the aforementioned compounds, and organic substances, for example stearic acid, malonic acid, ammonium salts of the aforementioned. acids, starches (e.g. potato starch and corn starch), cellulose, ground nutshells, finely ground polymer (e.g. polyethylene, polypropylene), etc.

In the preparation of the finely divided starting material A3 from the finely divided starting materials 1 and 2, appropriately in application terms, but not necessarily, finely divided shaping assistants are used.

These may already have been mixed into the two finely divided starting materials A1 and A2 or into only one of the two finely divided starting materials A1, A2 before these finely divided starting materials are mixed.

It will be appreciated that the finely divided shaping assistants may also or only (not until this point) be mixed into the finely divided mixture of finely divided starting material A1 and finely divided starting material A2.

The group of the finely divided shaping assistants (especially when they comprise elements $Z^5$, the shaping assistants are used with a $d_{90}$ of >5 μm; they typically do not comprise any elements of the multielement oxide I other than oxygen) includes first the so-called anticaking agents.

These are finely divided materials which are used advantageously in application terms in order to very substantially suppress, in the course of mixing, for example, reagglomeration ("caking together") of particles within the starting material A1 and/or within the starting material A2, since such a reagglomeration might influence the effective particle diameter. A group of finely divided anticaking agents preferred in accordance with the invention is that of finely divided hydrophobized silicas, especially finely divided hydrophobized synthetic silicas (silicon dioxides). Synthetic silicas can be obtained firstly directly by pyrogenic means from sand and secondly by precipitation reactions from waterglass. Synthetic silicas in particular, owing to their surface OH groups, are hydrophilic, i.e. they are wetted by water. For example, reaction of these surface OH groups with chlorosilanes makes it possible to prepare hydrophobized products both from the fumed silicas and from the precipitated silicas. For example, the hydrophobization can be accomplished by reaction with dimethyldichlorosilane in the presence of water vapor at approx. 400° C. in a fluidized bed reactor (is preferably employed in the case of fumed silicas).

In the case of precipitated silicas in particular, the chlorosilane is added to the precipitation suspension at a temperature of from 50 to 90° C. while stirring vigorously. This is followed by filtration, washing to neutrality with water, drying of the filtercake and heat treatment at from 300 to 400° C. H. Brunner, D. Schutte, Chem. Ing. Techn. 89, 437 (1965) and DT 2435860 and DT 1117245 describe the preparation of hydrophobized fine silicas in detail. Commercial products of hydrophobized precipitated silicas are, for example, the SIPERNAT® brands.

Preferably in accordance with the invention, the finely divided anticaking agent Sipernat® D17 From Degussa or from EVONIK Industries is used. Based on its weight, Sipernat® D17 comprises about 2% by weight of chemically bound carbon and is not wetted by water. Its tapped density (to ISO 787-11) is 150 g/l. Its $d_{50}$ value is 10 μm (laser diffraction to ISO 13320-1) and the specific surface area (nitrogen adsorption to ISO 5794-1, Annex D) is 100 m²/g.

Advantageously, finely divided anticaking agent, for example Sipernat® D17, is mixed into the finely divided starting material A1 before it is mixed with the finely divided starting material A2 to give the finely divided starting material A3. In general, the amount of finely divided anticaking agent added is from 0.1 to 3% by weight, based on the weight of the finely divided starting material A1.

The addition of anticaking agent also reduces the energy input required for homogeneous mixing of the two starting materials A1 and A2, which has an advantageous effect especially on obtaining the particle size of the finely divided starting material A2 in the course of mixing.

When the inventive shaping of the finely divided starting material A3 to give the geometric shaped bodies V is effected advantageously in accordance with the invention by compaction (or compression), it is appropriate in application terms to add lubricants as further finely divided shaping assistants to the finely divided starting material A3, for example graphite, carbon black, polyethylene glycol, polyacrylic acid, stearic acid, starch, mineral oil, vegetable oil, water, boron trifluoride and/or boron trinitride. Descriptions of additional use of lubricants in the context of a corresponding shaping can be found, for example, in documents DE-A 102007004961, WO 2005/030393, US-A 2005/0131253, WO 2007/017431, DE-A 102007005606 and in German application 102008040093.9. Preference is given in accordance with the invention to using exclusively finely divided graphite as a lubricant. Graphites added with preference are Asbury 3160 and Asbury 4012 from Asbury Graphite Mills, Inc. N.J. 08802, USA, and Timrex® T44 from Timcal Ltd., 6743 Bodio, Switzerland.

Advantageously, the finely divided graphite (typical $d_{90}$ values of graphites suitable in accordance with the invention are from 30 to 300 μm) is added first to the mixture of finely divided starting material A1 and finely divided starting material A2. However, it can also be mixed into each of the two finely divided starting materials A1, A2 (or only into one of the two) before the mixing thereof. Based on the weight of the finely divided starting material A3, it may comprise, for example, up to 15% by weight of finely divided lubricant. Usually, the lubricant content in the finely divided starting material A3 is, however, ≦9% by weight, in many cases ≦5% by weight, often ≦4% by weight; this is especially true when the finely divided lubricant is graphite. In general, the aforementioned added amount is ≧0.5% by weight, usually ≧2.5% by weight.

If required, further shaping assistants which may also be added to the finely divided starting material A3 are also finely divided reinforcing agents such as microfibers of glass, asbestos, silicon carbide or potassium titanate, which, after the shaping by compaction has ended, have a beneficial effect on the integrity of the resulting compact (of the resulting shaped body V).

In the course of the inventive thermal treatment of the shaped bodies V, from which the shaped catalyst bodies K accrue, additionally used shaping assistants may either remain in the resulting shaped catalyst body K or escape therefrom at least partly in gaseous form as a result of thermal and/or chemical decomposition to gaseous compounds (e.g. $CO$, $CO_2$). Shaping assistants which remain in the shaped catalyst body K, in the course of catalytic use thereof, have an essentially exclusively diluting action on the multielement oxide I active material.

In general, the finely divided starting material A3 is compacted to the desired geometry of the shaped body V (of the geometric shaped catalyst precursor body) through the action of external forces (pressure) on the finely divided precursor mixture. The shaping apparatus to be employed and the shaping method to be employed are not subject to any restriction.

For example, the compactive shaping can be effected by extrusion or tableting. In this case, the finely divided starting material A3 is preferably used dry to the touch. However, it may comprise, for example, up to 10% by weight of its total weight of added substances which are liquid under standard conditions (25° C., 1 atm). It is also possible for the finely divided starting material A3 to comprise solid solvates (e.g. hydrates) which contain such liquid substances in chemically and/or physically bound form. It will be appreciated, however, that the finely divided starting material A3 may also be entirely free of such substances.

A shaping process preferred in accordance with the invention for compacting the finely divided starting material A3 is tableting. The basics of tableting are described, for example, in "Die Tablette", Handbuch der Entwicklung, Herstellung and Qualitätssicherung ["The Tablet", Handbook of Development, Production and Quality Assurance], W. A. Ritschel and A. Bauer-Brandl, 2nd edition, Edition Verlag Aulendorf, 2002, and can be applied in an entirely corresponding manner to a tableting process according to the invention.

Advantageously, an inventive tableting is performed as described in the documents WO 2005/030393, German application 102008040093.9, German application 102008040094.7 and WO 2007/017431.

Instead of compacting the finely divided starting material A3 as such directly to the desired geometry of the shaped body V (in a single compaction step), it is frequently appropriate in accordance with the invention to perform, as the first shaping step, first an intermediate compaction in order to coarsen the finely divided starting material A3 (generally to particle diameters of from 100 to 2000 μm, preferably from 150 to 1500 μm, more preferably from 400 to 1250 μm, or from 400 to 1000 μm, or from 400 to 800 μm).

Even before the intermediate compaction, it is possible to add, for example, finely divided lubricant (e.g. graphite). Subsequently, the final shaping is effected on the basis of the coarsened powder, if required with addition beforehand once again, for example, of finely divided lubricant (e.g. graphite) and if appropriate further shaping and/or reinforcing assistants.

Just like the shaping apparatus for use to compact the finely divided starting material A3 and the shaping method to be employed, the desired geometry of the resulting shaped bodies V in the process according to the invention is not subject to any restriction either. In other words, the shaped catalyst precursor bodies (the shaped bodies V) may either have a regular or irregular shape, preference being given in accordance with the invention generally to regularly shaped bodies V.

For example, the shaped body V in the process according to the invention may have spherical geometry. In this case, the sphere diameter may, for example, be from 2 to 10 mm, or from 4 to 8 mm. The geometry of the shaped catalyst precursor body (of the shaped body V) may, however, also be solid cylindrical or hollow cylindrical (annular). In both cases, external diameter (E) and height (H) may, for example, be from 2 to 10 mm, or from 2 or 3 to 8 mm. In the case of hollow cylinders (rings), a wall thickness of from 1 to 3 mm is generally appropriate. It will be appreciated that useful catalyst precursor geometries also include those disclosed and recommended in WO 02/062737. In the case of solid cylinders, the external diameter may also be from 1 to 10 mm.

The shaping pressures employed in the course of compaction of finely divided starting material A3 will, in the process according to the invention, generally be from 50 kg/cm$^2$ to 5000 kg/cm$^2$. The shaping pressures are preferably from 200 to 3500 kg/cm$^2$, more preferably from 600 to 25 000 kg/cm$^2$.

Especially in the case of annular shaped bodies V, the shaping compaction in the process according to the invention, following the teaching of the documents German application 102008040093.9, German application 102008040094.7 and WO 2005/030393, shall be carried out in such a way that the side crushing strength SCS of the resulting annular shaped body V is 12 N≦SCS≦25 N. SD is preferably ≧13 N and ≦24 N, or ≧14 N and ≦22 N, and most preferably ≧15 N and ≦20 N.

The experimental determination of the side crushing strength is carried out as described in the documents WO 2005/030393 and WO 2007/017431. It will be appreciated that ringlike shaped bodies V, as recommended by German application 102008040093.9, are very particularly preferred in accordance with the invention. The end face of annular or ringlike shaped bodies V may either be curved or uncurved in the process according to the invention (cf. especially DE-A 102007004961, EP-A 184 790 and German application 102008040093.9). In determining the height of such geometric shaped bodies V, such curvature is not taken into account.

Shaped catalyst bodies K which are obtainable in accordance with the invention and have been produced by thermal treatment of shaped bodies V which have been obtained by compaction of finely divided starting material A3 are referred to as unsupported catalysts (shaped unsupported catalyst bodies K).

Ring geometries of shaped bodies V obtainable by compacting finely divided starting material A3 which are particularly advantageous in accordance with the invention satisfy the condition H/E=0.3 to 0.7. More preferably, H/E=0.4 to 0.6.

It is additionally favorable in accordance with the invention for the aforementioned annular shaped bodies V when the I/E ratio (where I is the internal diameter of the ring geometry) is from 0.3 to 0.7, preferably from 0.4 to 0.7.

Aforementioned ring geometries are particularly advantageous when they simultaneously have one of the advantageous H/E ratios and one of the advantageous I/E ratios. Such possible combinations are, for example, H/E=0.3 to 0.7 and I/E=0.3 to 0.8 or 0.4 to 0.7. Alternatively, H/E may be from 0.4 to 0.6, and I/E may simultaneously be from 0.3 to 0.8 or from 0.4 to 0.7. It is also favorable for the relevant ring geometries when H is from 2 to 6 mm and preferably from 2 to 4 mm. It is additionally advantageous when E for the rings is from 4 to 8 mm, preferably from 4 to 6 mm. The wall thickness of ring geometries preferred in accordance with the invention is from 1 to 1.5 mm.

Possible ring geometries for aforementioned annular shaped bodies V are thus (A×H×I) 5 mm×2 mm×2 mm, or 5 mm×3 mm×2 mm, or 5 mm×3 mm×3 mm, or 5.5 mm×3 mm×3.5 mm, or 6 mm×3 mm×4 mm, or 6.5 mm×3 mm×4.5 mm, or 7 mm×3 mm×5 mm, or 7 mm×7 mm×3 mm, or 7 mm×7 mm×4 mm.

The thermal treatment of inventive shaped bodies V (especially annular shaped bodies V; everything which follows applies especially to their thermal treatment) to obtain the geometric shaped catalyst bodies K is effected, in the process according to the invention, generally at temperatures (in this document, this generally means the temperature within the calcination material) which exceed 350° C. Normally, in the course of the thermal treatment, the temperature of 650° C. is, however, not exceeded. Advantageously in accordance with the invention, in the course of thermal treatment, the temperature of 600° C., preferably the temperature of 550° C. and more preferably the temperature of 500° C. will not be exceeded.

In addition, in the course of the thermal treatment of the shaped bodies V, preferably the temperature of 380° C., advantageously the temperature of 400° C., particularly advantageously the temperature of 420° C. and most preferably the temperature of 440° C. will not be exceeded. At the same time, the thermal treatment can also be divided into several sections over the course of its duration. For example, a thermal treatment can first be carried out at a temperature (phase 1) of from 150 to 350° C., preferably from 220 to 290° C., and then a thermal treatment at a temperature (phase 2) of from 400 to 600° C., preferably from 430 to 550° C.

Normally, the thermal treatment of the shaped bodies V takes several hours (frequently more than 5 h). In many cases, the total duration of the thermal treatment extends to more than 10 h. Usually, in the course of the thermal treatment of the shaped bodies V, treatment times of 45 h or 25 h are not exceeded. The total treatment time is often below 20 h. In principle, the thermal treatment can be carried out at higher temperatures over a shorter treatment time or at not excessively high temperatures over a longer treatment time. In an embodiment of the thermal treatment of the shaped bodies V which is advantageous in accordance with the invention, 465° C. is not exceeded and the treatment time in the ≧440° C. temperature window extends to from >10 to 20 h.

In all examples and comparative examples, the end calcination is effected at end calcination temperatures of ≦490° C., especially ≦475° C. One reason for this is that, on the commercial scale, within the higher end calcination temperature range, the energy expenditure and, in the case of end calcination in the presence of air, the risk of graphite fires, increase to a greater than proportional degree. Moreover, the long-term stability of the resulting geometric shaped catalyst bodies K may suffer from too high an end calcination temperature and/or end calcination time. In a further embodiment which is advantageous in accordance with the invention of the thermal treatment of the shaped bodies V, 465° C. (but not 490° C.) is exceeded and the treatment time in the temperature window of ≧465° C. extends to from 2 to 10 h.

In principle, however, all examples and comparative examples can also be carried out under otherwise unchanged conditions addressed or executed in this document at an end calcination temperature of 430° C., or 432° C., or 434° C., or 436° C., or 438° C., or 440° C., or 442° C., or 444° C., or 446° C., or 448° C., or 450° C., or 452° C., or 454° C., or 456° C., or 458° C., or 460° C., or 462° C., or 464° C., or 466° C., or 468° C., or 470° C., or 472° C., or 474° C. or 475° C.

The end calcination in all working examples B1 to B13 and in all comparative examples V1 to V16 (including the subsequent use as catalysts for the propene partial oxidation) can, however, also be carried out under otherwise unchanged conditions over an end calcination time shortened to 9, or 8, or 7, or 6, or 5, or 4, or 3, or 2, or 1 h, at an end calcination temperature increased in each case by 2, or 4, or 6, or 8, or 10, or 12, or 14, or 16, or 20° C.

The thermal treatment (including phase 1 (also referred to as decomposition phase)) of the shaped bodies V can be effected either under inert gas or under an oxidative atmosphere, for example air (or another mixture of inert gas and oxygen), or else under reducing atmosphere (for example a mixture of inert gas, NH$_3$, CO and/or H$_2$, or under methane, acrolein, methacrolein). Of course, the thermal treatment can also be performed under reduced pressure. It is also possible to vary the calcination atmosphere over the calcination time.

Preferably in accordance with the invention, the thermal treatment of the shaped bodies V is effected in an oxidizing atmosphere. Appropriately in application terms, the atmosphere consists predominantly of stationary or moving air. However, it may likewise (for example in the case of all examples and comparative examples) consist of a stationary or moving mixture of 25% by volume of $N_2$ and 75% by volume of air, or 50% by volume of $N_2$ and 50% by volume of air, or 75% by volume of $N_2$ and 25% by volume of air, or 100% by volume of $N_2$ (especially in the case of the examples and comparative examples addressed or executed in this document).

In principle, the thermal treatment of the shaped bodies V can be effected in a wide variety of different oven types, for example heatable forced-air chambers (forced-air ovens), tray ovens, rotary tube ovens, belt calciners or shaft ovens. Advantageously in accordance with the invention, the thermal treatment of the shaped bodies V is effected in a belt calcining apparatus, as recommended by DE-A 10046957 and WO 02/24620. This very substantially prevents hotspot formation within the calcination material, by virtue of increased volume flows of calcination atmosphere being conveyed through the calcination material through a gas-permeable conveyor belt which bears the calcination material with the aid of ventilators.

The thermal treatment of the shaped bodies V below 350° C. generally pursues the aim of thermal decomposition of the sources of the elements (of the elemental constituents), present in the shaped bodies V, of the desired multielement oxide I active material of the shaped catalyst bodies K and of any additionally used shaping assistants. This decomposition phase is frequently effected in the course of heating the calcination material to temperatures of $\geq 350°$ C.

In principle, the thermal treatment can be effected as described in US 2005/0131253.

Typically, the side crushing strengths of annular shaped unsupported catalyst bodies K obtainable in accordance with the invention as described are from 5 to 13 N, frequently from 8 to 11 N.

Shaped unsupported catalyst bodies K produced in accordance with the invention need not necessarily be used as such as catalysts for heterogeneously catalyzed partial gas phase oxidations of alkanes, alkanols, alkenes and/or alkenals having from 3 to 6 carbon atoms. Instead, they can also be subjected to grinding and the resulting finely divided material (if appropriate after classification of the resulting finely divided material) can be applied with the aid of a suitable liquid binder (e.g. water) to the surface of a suitable, for example spherical or annular, support body (geometric shaped support body) (for example employing the process principle disclosed in DE-A 2909671 and DE-A 100 51 419). After drying or immediately after application of the active material coating to the support body, the resulting coated catalyst can be used as a catalyst for aforementioned heterogeneously catalyzed gas phase partial oxidations, as described, for example, by WO 02/49757 and DE-A 10122027 for similar active materials.

The support materials used in the above procedure may be customary porous or nonporous aluminum oxides, silicon dioxide, zirconium dioxide, silicon carbide, or silicates such as magnesium or aluminum silicate. The support bodies may have a regular or irregular shape, preference being given to regularly shaped support bodies with distinct surface roughness (for example the spheres or rings already mentioned). It is particularly advantageous to use essentially nonporous, rough-surface rings made of steatite, whose longest dimension (longest direct straight line connecting two points on the surface of the shaped support body) is typically from 2 to 12 mm, frequently from 4 to 10 mm (cf. also DE-A 4442346).

The aforementioned longest dimensions are also useful for other shaped support bodies, for example spheres, solid cylinders and other rings.

The layer thickness of the active material coating (powder material) applied to the shaped support body will appropriately be selected within the range from 10 to 1000 µm, preferably in the range from 100 to 700 µm and more preferably in the range from 300 to 500 µm. Possible coating thicknesses are also from 10 to 500 µm or from 200 to 300 µm. The surface roughness $R_z$ of the shaped support body is frequently in the range from 40 to 200 µm, in many cases in the range from 40 to 100 µm (determined to DIN 4768 sheet 1 with a "Hommel Tester for DIN-ISO surface parameters" from Hommelwerke, Germany). Appropriately, the support material is nonporous (total volume of the pores based on the volume of the support body $\leq 1\%$ by volume).

In principle, the shaping (compaction) of the finely divided starting material A3 to a shaped body V can also be effected by applying the finely divided starting material A3 with the aid of a suitable liquid binder to the surface of a geometric shaped support body as described above. After drying, the resulting shaped precursor bodies V can be treated thermally in the inventive manner to obtain inventive shaped coated catalyst bodies K.

It is also possible to use active material powder obtained by grinding shaped unsupported catalyst bodies K produced in accordance with the invention as such in a fluidized or moving bed for the heterogeneously catalyzed partial gas phase oxidations addressed in these documents.

Moreover, it is advantageous with regard to a very marked long-term stability of inventive geometric shaped catalyst bodies K (especially when they are used as catalysts for the heterogeneously catalyzed partial gas phase oxidation of propene to acrolein or of isobutene to methacrolein) when, in addition to the inventive condition for the stoichiometric coefficient c, the magnitude F (the stability value F of the geometric shaped catalyst body K) of the product $$(d_{50}^{A1})^{0.7} \cdot (d_{90}^{A2})^{1.5} \cdot (p/2)^{-1}$$

is $\geq 820$, where the two diameters $d_{50}^{A1}$, $d_{90}^{A2}$ should be used in the length unit µm to form the product.

Preferably in accordance with the invention, $F \geq 830$, preferably $\geq 840$ and even better $\geq 850$.

Particularly advantageously, $F \geq 870$ or $\geq 900$, and, particularly advantageously, $F \geq 950$ or $\geq 1000$. Very particularly advantageously, $F \geq 1050$, or $\geq 1100$ or $\geq 1500$, or $\geq 2000$.

Taking account of the stated aim of a satisfactory starting selectivity of target product formation as early as on startup of the catalyst bed, F is preferably $\leq 5000$ or $\leq 4000$, sometimes $\leq 2500$, or $\leq 2400$ or $\leq 2200$.

Favorable values for F are also those which are $\leq 2000$, or $\leq 1800$, or $\leq 1600$ or $\leq 1500$.

In other words, values of F advantageous in accordance with the invention are $5000 \geq F \geq 1000$, or $4000 \geq F \geq 2000$, or $2500 \geq F \geq 850$, or $2450 \geq F \geq 900$, or $2400 \geq F \geq 950$.

Values for F which are particularly advantageous in accordance with the invention are $1900 \geq F \geq 1000$, or $1800 \geq F \geq 1050$.

Values of F which are very particularly advantageous in accordance with the invention are $1700 \geq F \geq 1100$, or $1500 \geq F \geq 1150$.

The long-term stability of inventive geometric shaped catalyst bodies K or of a catalyst bed comprising them is particularly marked when the activity which results in the course of formation is reduced as slowly as possible in the further operation of the partial oxidation. Periodically repeated regeneration processes, as recommended, for example, by documents WO 2005/42459 and WO 2005/49200, can additionally prolong the catalyst lifetime.

Increased stoichiometric coefficients c can reduce the long-term stability of inventive geometric shaped catalyst bodies K. Increased values for $d_{50}^{A1}$, $d_{50}^{A2}$ and $d_{90}^{A2}$ and reduced stoichiometric coefficients p have the opposite effect.

The inventive bismuth doping allows $d_{50}^{A1}$, $d_{50}^{A2}$ and $d_{90}^{A2}$ to assume comparatively greater values and the stoichiometric coefficient p to assume comparatively smaller values, without causing any significant losses in the starting activity and starting selectivity. Overall, comparatively elevated values for F and F* are thus achievable with both satisfactory starting activity and satisfactory starting selectivity.

If, in the process according to the invention, in addition to the condition for the value F, the condition is satisfied for the value F* of the product (the particle diameters $d_{50}^{A1}$ (of the finely divided starting material A1), $d_{50}^{A2}$ (of the finely divided starting material A2) again being reported in the length unit μm)

$$(d_{50}^{A1})^{0.7} \cdot (d_{50}^{A2})^{0.7} \cdot (p/2)^{-1}$$

that $F^* \geq 15$ (preferably $\geq 18$), more preferably 35 or $25 \geq F^* \geq 18$, this is additionally advantageous compared with the statements which have already been made so far.

The shaped catalyst bodies K obtainable in accordance with the invention are suitable as catalysts for all heterogeneously catalyzed gas phase oxidations for which the geometric shaped catalyst bodies $K^S$ have already been mentioned as suitable within this document. Geometric shaped catalyst bodies K obtainable in accordance with the invention are, however, particularly suitable as catalysts for the partial oxidations of propene to acrolein and of isobutene and/or tert-butanol to methacrolein. This is especially true of inventive annular shaped unsupported catalyst bodies K. The partial oxidation can be carried out, for example, as described in documents DE-A 102007004961, WO 02/49757, WO 02/24620, German application 102008040093.9, WO 2005/030393, EP-A 575 897, WO 2007/082827, WO 2005/113127, WO 2005/047224, WO 2005/042459 and WO 2007/017431.

The ring geometries emphasized individually in this document of the annular unsupported catalysts obtainable as described are also found to be advantageous especially when the loading of the catalyst charge with propene, isobutene and/or tert-butanol (or methyl ether thereof) present in the starting reaction gas mixture is $\geq 130$ l (STP)/l of catalyst charge·h (upstream and/or downstream beds of inert material are not considered as belonging to the catalyst charge in this document in considerations of loading).

However, annular shaped unsupported catalyst bodies K obtainable as described still have this advantage when the aforementioned loading of the catalyst charge is $\geq 140$ l (STP)/l·h, or $\geq 150$ l (STP)/l·h, or $\geq 160$ l (STP)/l·h. Normally, the aforementioned loading of the catalyst charge will be $\leq 600$ l (STP)/l·h, frequently $\leq 500$ l (STP)/l·h, in many cases $\leq 400$ l (STP)/l·h or $\leq 350$ l (S-TP)/l·h. Loadings in the range from 160 l (STP)/l·h to 300 or 250 or 200 l (STP)/l·h are particularly appropriate.

It will be appreciated that the annular shaped unsupported catalyst bodies K obtainable as described can be operated in a manner advantageous in accordance with the invention as catalysts for the partial oxidation of propene to acrolein or of isobutene and/or tert-butanol (or methyl ether thereof) to methacrolein also at loadings of the catalyst charge with the starting compound to be oxidized partially of $\leq 130$ l (STP)/l·h, or $\leq 120$ l (STP)/l·h, or $\leq 110$ l (STP)/l·h. In general, this loading will, however, be at values of $\geq 60$ l (STP)/l·h, or $\geq 70$ l (STP)/l·h, or $\geq 80$ l (STP)/l·h.

In principle, the loading of the catalyst charge with the starting compound to be oxidized partially (propene, isobutene and/or tert-butanol (or methyl ether thereof)) can be adjusted by means of two adjusting screws:

the loading of the catalyst charge with starting reaction gas mixture (the reaction gas mixture which is supplied to the fixed catalyst bed), and/or the content in the starting reaction gas mixture of the starting compound to be oxidized partially.

The shaped unsupported catalyst bodies K, for example annular shaped unsupported catalyst bodies K, obtainable in accordance with the invention are suitable especially when the loading is adjusted in particular by means of the aforementioned adjusting screw a) at loadings of the catalyst charge with the organic compound to be oxidized partially of above 130 l (STP)/l·h.

The propene content (isobutene content or tert-butanol content (or methyl ether content)) in the starting reaction gas mixture will generally (i.e. essentially irrespective of the loading) be from 4 to 20% by volume, frequently from 5 to 15% by volume, or from 5 to 12% by volume, or from 5 to 8% by volume (based in each case on the total volume of the starting reaction gas mixture).

Frequently, the gas phase partial oxidation process of the partial oxidation catalyzed by the shaped unsupported catalyst bodies K, for example annular shaped unsupported catalyst bodies K, obtainable as described (or other geometric shaped catalyst bodies K) will be performed (essentially irrespective of the loading) at a volume ratio of (organic) compound to be oxidized partially (e.g. propene):oxygen:inert gases (including water vapor) in the starting reaction gas mixture of 1:(1.0 to 3.0):(5 to 25), preferably 1:(1.5 to 2.3):(10 to 20).

Inert gases refer to those gases which remain chemically unchanged in the course of the partial oxidation to an extent of at least 95 mol %, preferably to an extent of at least 98 mol %.

In the above-described starting reaction gas mixtures, the inert gas may consist of molecular nitrogen to an extent of $\geq 20\%$ by volume, or to an extent of $\geq 30\%$ by volume, or to an extent of $\geq 40\%$ by volume, or to an extent of $\geq 50\%$ by volume, or to an extent of $\geq 60\%$ by volume, or to an extent of $\geq 70\%$ by volume or to an extent of $\geq 80\%$ by volume, or to an extent of $\geq 90\%$ by volume or to an extent of $\geq 95\%$ by volume.

However, when the loadings of the catalyst charge with the organic compound to be partially oxidized are $\geq 150$ l (STP)/l·h, it is advisable to use inert diluent gases such as propane, ethane, methane, pentane, butane, $CO_2$, CO, water vapor and/or noble gases for the starting reaction gas mixture. Generally, these inert gases and their mixtures may also be used even at lower loadings of the catalyst charge with the organic compound to be partially oxidized. Cycle gas may also be used as a diluent gas. Cycle gas refers to the residual gas which remains when the target compound is substantially selectively removed from the product gas mixture of the partial oxidation. It has to be taken into account that the partial oxidations to acrolein or methacrolein using the shaped catalyst bodies K, for example annular shaped catalyst bodies K, obtainable in accordance with the invention may only be the first stage of a two-stage partial oxidation to acrylic acid or methacrylic acid as the actual target compounds, in which case the cycle gas is not usually formed until after the second stage. In such a two-stage partial oxidation, the product gas mixture of the first stage is generally fed as such, optionally after cooling and/or secondary oxygen addition, to the second partial oxidation stage.

In the partial oxidation of propene to acrolein using the shaped catalyst bodies K, for example annular shaped catalyst bodies K, obtainable as described, a typical composition of the starting reaction gas mixture measured at the reactor inlet (irrespective of the loading selected) may comprise, for example, the following components:
from 6 to 6.5% by volume of propene,
from 1 to 3.5% by volume of $H_2O$,
from 0.2 to 0.5% by volume of CO,
from 0.6 to 1.2% by volume of $CO_2$,
from 0.015 to 0.04% by volume of acrolein,
from 10.4 to 11.3% by volume of $O_2$ and,
as the remainder ad 100% by volume, molecular nitrogen,
or:
5.6% by volume of propene,
10.2% by volume of oxygen,
1.2% by volume of $CO_x$,
81.3% by volume of $N_2$ and
1.4% by volume of $H_2O$.

The former compositions are suitable especially at propene loadings of $\geq 130$ l (STP)/l·h and the latter composition especially at propene loadings of <130 l (STP)/l·h, especially $\leq 100$ l (STP)/l·h, of the fixed catalyst bed.

As alternative compositions of the starting reaction gas mixture, useful compositions (irrespective of the loading selected) are those which have the following components:
from 4 to 25% by volume of propene,
from 6 to 70% by volume of propane,
from 5 to 60% by volume of $H_2O$,
from 8 to 65% by volume of $O_2$, and
from 0.3 to 20% by volume of $H_2$;
or
from 4 to 25% by volume of propene,
from 6 to 70% by volume of propane,
from 0 to 60% by volume of $H_2O$,
from 8 to 16% by volume of $O_2$,
from 0 to 20% by volume of $H_2$
from 0 to 0.5% by volume of CO;
from 0 to 1.2% by volume of $CO_2$;
from 0 to 0.04% by volume of acrolein;
as the remainder ad 100% by volume, essentially $N_1$;
or
from 50 to 80% by volume of propane,
from 0.1 to 20% by volume of propene,
from 0 to 10% by volume of $H_2$,
from 0 to 20% by volume of $N_2$,
from 5 to 15% by volume of $H_2O$, and
sufficient molecular oxygen that the molar ratio of oxygen content to propene content is from 1.5 to 2 5;
or
from 6 to 9% by volume of propene,
from 8 to 18% by volume of molecular oxygen,
from 6 to 30% by volume of propane, and
from 32 to 72% by volume of molecular nitrogen.

However, the starting reaction gas mixture may also have the following composition:
from 4 to 15% by volume of propene,
from 1.5 to 30% by volume (frequently from 6 to 15% by volume) of water,
from $\geq 0$ to 10% by volume (preferably from $\geq 0$ to 5% by volume) of constituents other than propene, water, oxygen and nitrogen, and sufficient molecular oxygen that the molar ratio of molecular oxygen present to molecular propene present is from 1.5 to 2.5, and, as the remainder up to 100% by volume of the total amount, molecular nitrogen.

Another possible starting reaction gas mixture composition may comprise:
6.0% by volume of propene,
60% by volume of air and
34% by volume of $H_2O$.

Alternatively, starting reaction gas mixtures of the composition according to Example 1 of EP-A 990 636, or according to Example 2 of EP-A 990 636, or according to Example 3 of EP-A 1 106 598, or according to Example 26 of EP-A 1 106 598, or according to Example 53 of EP-A 1 106 598, may also be used.

The shaped catalyst bodies K, for example annular shaped catalyst bodies K, obtainable as described are also suitable for the processes of DE-A 10246119 and DE-A 10245585.

Further starting reaction gas mixtures which are suitable in accordance with the invention may lie within the following composition framework:
from 7 to 11% by volume of propene,
from 6 to 12% by volume of water,
from $\geq 0$ to 5% by volume of constituents other than propene, water, oxygen and nitrogen,
sufficient molecular oxygen that the molar ratio of molecular oxygen present to propene present is from 1.6 to 2.2, and
as the remainder up to 100% by volume of the total amount of molecular nitrogen.

In the case of methacrolein as the target compound, the starting reaction gas mixture may in particular have the composition described in DE-A 44 07 020.

The reaction temperature for the propene partial oxidation when the shaped catalyst bodies K, for example annular shaped catalyst bodies K, obtainable as described are used is frequently from 300 to 380° C. The same also applies in the case of methacrolein as the target compound.

The reaction pressure for the aforementioned partial oxidations is generally from 0.5 or 1.5 to 3 or 4 bar (what are always meant in this document, unless explicitly stated otherwise, are absolute pressures).

The total loading of the catalyst charge with starting reaction gas mixture in the aforementioned partial oxidations typically amounts to from 1000 to 10 000 l (STP)/l·h, usually to from 1500 to 5000 l (STP)/l·h and often to from 2000 to 4000 l (STP)/l·h.

The propene to be used in the starting reaction gas mixture is in particular polymer-grade propene and chemical-grade propene, as described, for example, in DE-A 102 32 748.

The oxygen source used is normally air.

In the simplest case, the partial oxidation employing the shaped catalyst bodies K, for example annular shaped catalyst bodies K, obtainable as described may be carried out, for example, in a one-zone multiple catalyst tube fixed bed reactor, as described by DE-A 44 31 957, EP-A 700 714 and EP-A 700 893.

Typically, the catalyst tubes in the aforementioned tube bundle reactors are manufactured from ferritic steel and typically have a wall thickness of from 1 to 3 mm. Their internal diameter is generally from 20 to 30 mm, frequently from 21 to 26 mm. A typical catalyst tube length is, for example, 3.20 m. It is appropriate from an application point of view for the number of catalyst tubes accommodated in the tube bundle vessel to be at least 1000, preferably at least 5000. Frequently, the number of catalyst tubes accommodated in the reaction vessel is from 15 000 to 35 000. Tube bundle reactors having a number of catalyst tubes above 40 000 are usually exceptional. Within the vessel, the catalyst tubes are normally arranged in homogeneous distribution, and the distribution is appropriately selected in such a way that the separation of the central internal axes from immediately adjacent catalyst tubes (known as the catalyst tube pitch) is from 35 to 45 mm (cf. EP-B 468 290).

However, the partial oxidation may also be carried out in a multizone (for example two-zone) multiple catalyst tube fixed bed reactor, as recommended by DE-A 199 10 506, DE-A 103 13 213, DE-A 103 13 208 and EP-A 1 106 598, especially at elevated loadings of the catalyst charge with the organic compound to be partially oxidized. A typical catalyst tube length in the case of a two-zone multiple catalyst tube fixed bed reactor is 3.50 m. Everything else is substantially as described for the one-zone multiple catalyst tube fixed bed reactor. Around the catalyst tubes, within which the catalyst charge is disposed, a heat exchange medium is conducted in each heating zone. Useful such media are, for example, melts of salts such as potassium nitrate, potassium nitrite, sodium nitrite and/or sodium nitrate, or of low-melting metals such as sodium, mercury and also alloys of different metals. The flow rate of the heat exchange medium within the particular heating zone is generally selected in such a way that the temperature of the heat exchange medium rises from the entry point into the temperature zone to the exit point from the temperature zone by from 0 to 15° C., frequently from 1 to 10° C., or from 2 to 8° C., or from 3 to 6° C.

The inlet temperature of the heat exchange medium which, viewed over the particular heating zone, may be conducted in cocurrent or in countercurrent to the reaction gas mixture is preferably selected as recommended in the documents EP-A 1 106 598, DE-A 199 48 523, DE-A 199 48 248, DE-A 103 13 209, EP-A 700 714, DE-A 103 13 208, DE-A 103 13 213, WO 00/53557, WO 00/53558, WO 01/36364, WO 00/53557 and also the other documents cited as prior art in this document. Within the heating zone, the heat exchange medium is preferably conducted in a meandering manner. In general, the multiple catalyst tube fixed bed reactor addition ally has thermal tubes for determining the gas temperature in the catalyst bed. Appropriately, the internal diameter of the thermal tubes and the diameter of the internal accommodating sleeve for the thermal element are selected in such a way that the ratio of volume developing heat of reaction to surface area removing heat for the thermal tubes and working tubes is the same or only slightly different.

The pressure drop in the case of working tubes and thermal tubes, based on the same GHSV, should be the same. A pressure drop may be equalized in the case of the thermal tube by adding spalled catalyst to the shaped catalyst bodies. This equalization is appropriately effected homogeneously over the entire thermal tube length.

To prepare the catalyst charge in the catalyst tubes, as already mentioned, it is possible only to use shaped catalyst bodies K, for example annular shaped catalyst bodies K, obtainable as described or, for example also substantially homogeneous mixtures of shaped catalyst bodies K, for example annular shaped catalyst bodies K, obtainable as described and shaped bodies which have no active composition and behave substantially inertly with respect to the heterogeneously catalyzed partial gas phase oxidation. Useful materials for such inert shaped bodies include, for example, porous or nonporous aluminum oxides, silicon dioxide, zirconium dioxide, silicon carbide, silicates such as magnesium or aluminum silicate and/or steatite (for example of the C220 type from CeramTec, Germany).

The geometry of such inert shaped diluent bodies may in principle be as desired. In other words, they may be, for example, spheres, polygons, solid cylinders or else, as, for example, in the case of annular shaped catalyst bodies K, rings. Frequently, the inert shaped diluent bodies selected will be those whose geometry corresponds to that of the shaped catalyst bodies K to be diluted with them. However, along the catalyst charge, the geometry of the shaped catalyst body K may also be changed or shaped catalyst bodies K of different geometry may be used in a substantially homogeneous mixture. In a less preferred procedure, the active composition of the shaped catalyst body K may also be changed along the catalyst charge.

Quite generally, as already mentioned, the catalyst charge is advantageously configured in such a way that the volume-specific (i.e. normalized to the unit of the volume) activity either remains constant or increases (continuously, sharply or stepwise) in the flow direction of the reaction gas mixture.

A reduction in the volume-specific activity may be achieved in a simple manner, for example, by homogeneously diluting a basic amount of shaped catalyst bodies K, for example annular shaped catalyst bodies K, prepared uniformly in accordance with the invention with inert shaped diluent bodies. The higher the proportion of the shaped diluent bodies selected, the lower the active composition or catalyst activity present in a certain volume of the charge. However, a reduction can also be achieved by changing the geometry of the shaped catalyst bodies K obtainable in accordance with the invention in such a way that the amount of active composition present in the unit of the reaction tube internal volume becomes smaller.

For the heterogeneously catalyzed gas phase partial oxidations using annular shaped unsupported catalyst bodies K obtainable as described, the catalyst charge is preferably either configured uniformly with only one type of shaped unsupported catalyst body K over the entire length or structured as follows. At the reactor inlet is positioned, to a length of from 10 to 60%, preferably from 10 to 50%, more preferably from 20 to 40% and most preferably from 25 to 35% (i.e., for example, to a length of from 0.70 to 1.50 m, preferably from 0.90 to 1.20 m), in each case of the total length of the catalyst charge, a substantially homogeneous mixture of annular shaped unsupported catalyst body K obtainable in accordance with the invention and inert shaped diluent bodies (both preferably having substantially the same geometry), the proportion by weight of the shaped diluent bodies (the mass densities of shaped catalyst bodies K and of shaped diluent bodies generally differ only slightly) being normally from 5 to 40% by weight, or from 10 to 40% by weight, or from 20 to 40% by weight, or from 25 to 35% by weight. Downstream of this first charge section, there is then advantageously, up to the end of the length of the catalyst charge (i.e., for example, to a length of from 1.00 to 3.00 m or from 1.00 to 2.70 m, preferably from 1.40 to 3.00 m, or from 2.00 to 3.00 m), either a bed of the annular shaped unsupported catalyst body K obtainable as described which is diluted only to a lesser extent (than in the first section), or, most preferably, an unaccompanied (undiluted) bed of the same annular shaped unsupported catalyst body K which has also been used in the first section. Of course, a constant dilution may also be selected over the entire charge. Charging may also be effected in the first section using only an annular shaped unsupported catalyst body K obtainable in accordance with the invention and having lower active composition density based on its space demand, and, in the second section, using an annular shaped unsupported catalyst body K obtainable in accordance with the invention having higher active composition density based on its space demand (for example 6.5 mm×3 mm×4.5 mm [E×H×I] in the first section, and 5×2×2 mm in the second section).

Overall, in a partial oxidation for preparing acrolein or methacrolein carried out using the shaped catalyst bodies K, for example annular shaped catalyst bodies K, obtainable as described as catalysts, the catalyst charge, the starting reaction gas mixture, the loading and the reaction temperature are generally selected in such a way that, on single pass of the reaction gas mixture through the catalyst charge, a conversion of the organic compound to be partially oxidized (propene, isobutene, tert-butanol or its methyl ether) of at least 90 mol %, or at least 92 mol %, preferably of at least 94 mol %, results. The selectivity of acrolein or methacrolein formation will regularly be ≧80 mol %, or ≧85 mol %. Of course, very low hotspot temperatures are desired.

Finally, it is emphasized that annular shaped unsupported catalyst bodies K obtainable as described also have advantageous fracture behavior in the course of reactor charging.

A fresh catalyst charge (fixed catalyst bed) comprising geometric shaped catalyst bodies K obtainable in accordance with the invention can be started up, for example, as described in DE-A 103 37 788.

The forming of inventive geometric shaped catalyst bodies K can also be accelerated by performing it at essentially uniform conversion under increased loading of the catalyst charge with starting reaction gas mixture.

Otherwise, geometric shaped catalyst bodies K obtainable in accordance with the invention are quite generally suitable as catalysts with increased starting activity and increased target product formation selectivity for gas phase catalytic partial oxidations of alkanes (especially propane), alkanols, alkanals, alkenes and alkenals comprising from 3 to 6 (i.e. 3, 4, 5 or 6) carbon atoms to, for example, olefinically unsaturated aldehydes and/or carboxylic acids, and the corresponding nitriles (ammoxidation, in particular of propene to acrylonitrile and of 2-methylpropene or tert-butanol (or the methyl ether thereof) to methacrylonitrile), and for gas phase catalytic oxidative dehydrogenations of the aforementioned organic compounds comprising 3, 4, 5 or 6 carbon atoms.

Appropriately in application terms, inventive shaped catalyst bodies K (and all working examples B1 to B13 and comparative examples V1 to V16) are produced on the industrial scale as described in German applications 102008040093.9 and 102008040094.7 (particularly advantageously according to example I.3. of application 102008040094.7).

The present application thus comprises especially the following inventive embodiments:

A process for producing geometric shaped catalyst bodies K which comprise, as an active material, a multielement oxide I of the general stoichiometry I $$[Bi_a Z^1_b O_x]_p [Bi_c Mo_{12} Fe_d Z^2_e Z^3_f Z^4_g Z^5_h Z^6_i O_y]_1 \quad (I),$$

where $Z^1$=tungsten or tungsten and molybdenum, with the proviso that at least 10 mol % of the molar total amount of $Z^1$ is tungsten, $Z^2$=one element or more than one element from the group consisting of nickel and cobalt, $Z^3$=one element or more than one element from the group consisting of the alkali metals, the alkaline earth metals and thallium, $Z^4$=one element or more than one element from the group consisting of zinc, phosphorus, arsenic, boron, antimony, tin, cerium, vanadium and chromium, $Z^5$=one element or more than one element from the group consisting of silicon, aluminum, titanium, tungsten and zirconium, $Z^5$=one element or more than one element from the group consisting of copper, silver, gold, yttrium, lanthanum and the lanthanides, a=0.1 to 3,
b=0.1 to 10,
d=0.01 to 5,
e=1 to 10,
f=0.01 to 2,
g=0 to 5,
h=0 to 10,
i=0 to 1,
p=0.05 to 6, and x, y=numbers determined by the valency and frequency of the element in I other than oxygen, in which a finely divided mixed oxide $Bi_a Z^1_b O_x$ with a particle diameter $d_{50}^{A1}$, as starting material A1, is preformed with the proviso that 1 μm≦$d_{50}^{A1}$≦100 μm;

sources of the elements other than oxygen in the component $T=[Bi_c Mo_{12} Fe_d Z^2_e Z^3_f Z^4_g Z^5_h Z^6_i O_y]_1$ of the multielement oxide I are used in an aqueous medium to obtain an intimate aqueous mixture M, with the proviso that each of the sources used, in the course of preparation of the aqueous mixture M, passes through a degree of division Q for which its diameter $d_{90}^Q$ is ≦5 μm, and the aqueous mixture M comprises the elements Bi, Mo, Fe, $Z^2$, $Z^3$, $Z^4$, $Z^5$ and $Z^6$ in the stoichiometry I*

$$Bi_c Mo_{12} Fe_d Z^2_e Z^3_f Z^4_g Z^5_h Z^6_i \quad (I^*);$$

the aqueous mixture M, by means of drying and adjusting the degree of division $d_{90}^{A2}$, is used to obtain a finely divided starting material A2 with a particle diameter $d_{90}^{A2}$, with the proviso that 400 μm≧$d_{90}^{A2}$≧10 μm;

starting material A1 and starting material A2, or starting material A1, starting material A2 and finely divided shaping assistant, are mixed with one another to form a finely divided starting material A3, with the proviso that the starting material A3 comprises the elements other than oxygen introduced into the starting material A3 via starting materials A1 and A2 in the multielement oxide I in the stoichiometry I**

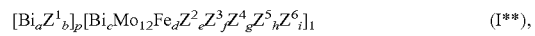

$$[Bi_a Z^1_b]_p [Bi_c Mo_{12} Fe_d Z^2_e Z^3_f Z^4_g Z^5_h Z^6_i]_1 \quad (I^{**}),$$

finely divided starting material A3 is used to form geometric shaped bodies V, and the shaped bodies V are treated thermally at elevated temperature to obtain the geometric shaped catalyst bodies K, wherein the stoichiometric coefficient c satisfies the condition 0<c≦0.8.

2. The process according to embodiment 1, wherein c is ≧0.001.

3. The process according to embodiment 1, wherein c is ≧0.002.

4. The process according to embodiment 1, wherein c is ≧0.005.

5. The process according to any one of embodiments 1 to 4, wherein c is ≦0.7.

6. The process according to any one of embodiments 1 to 4, wherein c is ≦0.6.

7. The process according to embodiment 1, wherein 0.007≦c≦0.5.

8. The process according to embodiment 1, wherein 0.01≦c≦0.4.

9. The process according to embodiment 1, wherein 0.02≦c≦0.3.

10. The process according to embodiment 1, wherein 0.03≦c≦0.2.

11. The process according to embodiment 1, wherein 0.04≦c≦0.1.

12. The process according to embodiment 1, wherein $0.005 \leq c \leq 0.08$.

13. The process according to embodiment 1, wherein $0.01 \leq c \leq 0.06$.

14. The process according to any one of embodiments 1 to 13, wherein p is 0.1 to 4.

15. The process according to any one of embodiments 1 to 13, wherein p is 0.2 to 3.

16. The process according to any one of embodiments 1 to 13, wherein p is 0.3 to 1.

17. The process according to any one of embodiments 1 to 16, wherein the $n_{Bi}:n_{Mo}$ ratio of the total molar amount of Bi present in the multielement oxide I, $n_{Bi}$, to the total molar amount of Mo present in the multielement oxide I, $n_{Mo}$, is 0.3 to 2:12.

18. The process according to embodiment 17, wherein $n_{Bi}:n_{Mo}$ is 0.4 to 1.8:12.

19. The process according to embodiment 17, wherein $n_{Bi}:n_{Mo}$ is 0.5 to 1.6:12.

20. The process according to any one of embodiments 1 to 19, wherein $1 \ \mu m \leq d_{50}^{A1} \leq 50 \ \mu m$.

21. The process according to any one of embodiments 1 to 19, wherein $1 \ \mu m \leq d_{50}^{A1} \leq 10 \ \mu m$.

22. The process according to any one of embodiments 1 to 19, wherein $1.5 \ \mu m \leq d_{50}^{A1} \leq 6 \ \mu m$.

23. The process according to any one of embodiments 1 to 19, wherein $2 \ \mu m \leq d_{50}^{A1} \leq 3 \ \mu m$.

24. The process according to any one of embodiments 1 to 23, wherein $200 \ \mu m \geq d_{90}^{A2} \geq 20 \ \mu m$.

25. The process according to any one of embodiments 1 to 23, wherein $150 \ \mu m \geq d_{90}^{A2} \geq 40 \ \mu m$.

26. The process according to any one of embodiments 1 to 23, wherein $100 \ \mu m \geq d_{90}^{A2} \geq 50 \ \mu m$.

27. The process according to any one of embodiments 1 to 26, wherein the particle diameter $d_{50}^{A2}$ of the finely divided starting material A2 satisfies the condition $10 \ \mu m \leq d_{50}^{A2} \leq 100 \ \mu m$.

28. The process according to any one of embodiments 1 to 26, wherein the particle diameter $d_{50}^{A2}$ of the finely divided starting material A2 satisfies the condition $20 \ \mu m \leq d_{50}^{A2} \leq 60 \ \mu m$.

29. The process according to any one of embodiments 1 to 28, wherein the ratio of the particle diameter $d_{90}^{A2}$ of the finely divided starting material A2 to the particle diameter $d_{10}^{A2}$ of the finely divided starting material A2 is in the range from 5 to 20.

30. The process according to any one of embodiments 1 to 29, wherein $d_{90}^{Q}$ for each of the sources used is $\leq 3 \ \mu m$.

31. The process according to any one of embodiments 1 to 29, wherein $d_{90}^{Q}$ for each of the sources used is $\leq 1 \ \mu m$.

32. The process according to any one of embodiments 1 to 29, wherein $d_{90}^{Q}$ for each of the sources used is $\leq 0.5 \ \mu m$.

33. The process according to any one of embodiments 1 to 32, wherein each of the sources used, in the course of preparation of the aqueous mixture M, passes through the state of a colloidal solution or of a true solution.

34. The process according to any one of embodiments 1 to 32, wherein the component T comprises the element Si and each of the sources of the elements other than silicon used, in the course of preparation of the aqueous mixture M, passes through the state of a true solution and the source of the element Si used is a silica sol.

35. The process according to any one of embodiments 1 to 34, wherein the finely divided starting material A2 is obtained by spray-drying the aqueous mixture M.

36. The process according to any one of embodiments 1 to 35, wherein $Z^2$=Co.

37. The process according to any one of embodiments 1 to 36, wherein $Z^3$=K, Cs and/or Sr.

38. The process according to any one of embodiments 1 to 37, wherein $Z^5$=Si.

39. The process according to any one of embodiments 1 to 38, wherein a is from 0.5 to 3.

40. The process according to any one of embodiments 1 to 38, wherein a is from 1.5 to 2.5.

41. The process according to any one of embodiments 1 to 40, wherein b is from 2 to 5.

42. The process according to any one of embodiments 1 to 40, wherein b is from 3 to 5.

43. The process according to any one of embodiments 1 to 42, wherein at least 20 mol % of the molar total amount of $Z^1$ is tungsten.

44. The process according to any one of embodiments 1 to 42, wherein at least 80 mol % of the molar total amount of $Z^1$ is tungsten.

45. The process according to any one of embodiments 1 to 42, wherein the molar total amount of $Z^1$ is tungsten.

46. The process according to any one of embodiments 1 to 45, wherein e is from 3 to 8.

47. The process according to any one of embodiments 1 to 45, wherein e is from 4 to 7.

48. The process according to any one of embodiments 1 to 47, wherein f is from 0.03 to 1.

49. The process according to any one of embodiments 1 to 48, wherein d is from 1 to 4.

50. The process according to any one of embodiments 1 to 49, wherein h is from 0.1 to 8.

51. The process according to any one of embodiments 1 to 49, wherein h is from 0.5 to 3.

52. The process according to any one of embodiments 1 to 51, wherein the finely divided mixed oxide $Bi_a Z^1_b O_x$ is the mixed oxide $Bi_2 W_4 O_{15}$.

53. The process according to any one of embodiments 1 to 52, wherein the value F of the product $$(d_{50}^{A1})^{0.7} \cdot (d_{90}^{A2})^{1.5} \cdot (p/2)^{-1}$$

is $\geq 820$, where the two particle diameters $d_{50}^{A1}$ and $d_{90}^{A2}$ should be reported in the length unit μm.

54. The process according to embodiment 53, wherein $1000 \leq F \leq 5000$.

55. The process according to embodiment 53, wherein $2000 \leq F \leq 4000$.

56. The process according to any one of embodiments 1 to 55, wherein the magnitude F* of the product $$(d_{50}^{A1})^{0.7} \cdot (d_{50}^{A2})^{0.7} \cdot (p/2)^{-1}$$

is $\geq 15$, where the two particle diameters $d_{50}^{A1}$ and $d_{50}^{A2}$ should be reported in the length unit μm.

57. The process according to embodiment 56, wherein $35 \geq F^* \geq 18$.

58. The process according to any one of embodiments 1 to 57, wherein finely divided starting material A1, finely divided starting material A2 and shaping assistant comprising finely divided hydrophobized silica are mixed with one another to give the finely divided starting material A3.

59. The process according to any one of embodiments 1 to 58, wherein finely divided starting material A1, finely divided starting material A2 and shaping assistant comprising finely divided graphite are mixed with one another to give the finely divided starting material A3.

60. The process according to any one of embodiments 1 to 59, wherein geometric shaped bodies V are formed with finely divided starting material A3 by compacting the finely divided starting material A3.

61. The process according to embodiment 60, wherein the compaction is effected by extrusion or tableting.

62. The process according to any one of embodiments 1 to 61, wherein the geometric shaped body V is a ring.

63. The process according to embodiment 62, wherein the side crushing strength SCS of the annular shaped body V satisfies the condition 12 N≦SCS≦25 N.

64. The process according to any one of embodiments 1 to 61, wherein the geometric shaped body V is a sphere.

65. The process according to any one of embodiments 1 to 61, wherein the geometric shaped body V is a solid cylinder.

66. The process according to embodiment 62 or 63, wherein the external diameter=from 2 to 10 mm, the height=from 2 to 10 mm and the wall thickness of the ring is from 1 to 3 mm.

67. The process according to embodiment 64, wherein the sphere diameter is from 2 to 10 mm.

68. The process according to embodiment 65, wherein the external diameter=from 1 to 10 mm and the height of the solid cylinder is from 2 to 10 mm.

69. The process according to any one of embodiments 1 to 59, wherein geometric shaped bodies V are formed with finely divided starting material A3 by applying the finely divided starting material A3 to the surface of a geometric shaped support body with the aid of a liquid binder.

70. The process according to any one of embodiments 1 to 69, wherein the temperature of 350° C. is exceeded and the temperature of 600° C. is not exceeded in the course of thermal treatment of the shaped bodies V.

71. The process according to any one of embodiments 1 to 69, wherein the temperature of 420° C. is exceeded and the temperature of 500° C. is not exceeded in the course of thermal treatment of the shaped bodies V.

72. The process according to any one of embodiments 1 to 71, wherein the thermal treatment is effected in the presence of air.

73. The process according to any one of embodiments 1 to 68 or according to any one of embodiments 70 to 72, wherein the shaped catalyst body K is a shaped unsupported catalyst body K and the process for preparing it is followed by a process for grinding to give finely divided material and the finely divided material is applied to the surface of a geometric shaped support body with the aid of a liquid binder.

74. A shaped catalyst body obtainable by a process according to any one of embodiments 1 to 73.

75. A catalyst obtainable by grinding a shaped catalyst body which is a shaped unsupported catalyst body and is obtainable by a process according to any one of embodiments 1 to 68.

76. A process for heterogeneously catalyzed partial gas phase oxidation of an alkane, alkanol, alkanal, alkene and/or alkenal which comprises from 3 to 6 carbon atoms over a catalyst bed, wherein said catalyst bed comprises a shaped catalyst body according to embodiment 74 or a catalyst according to embodiment 75.

77. The process according to embodiment 76, which is a process for heterogeneously catalyzed partial gas phase oxidation of propene to acrolein.

78. The process according to embodiment 76, which is a process for heterogeneously catalyzed partial gas phase oxidation of isobutene to methacrolein.

79. The process according to embodiment 76, which is a process for ammoxidation of propene to acrylonitrile or a process for ammoxidation of isobutene to methacrylonitrile.

80. The use of a shaped catalyst body according to embodiment 74 or of a catalyst according to embodiment 75 as a catalyst in a process for heterogeneously catalyzed partial gas phase oxidation of an alkane, alkanol, alkanal, alkene and/or alkenal comprising from 3 to 6 carbon atoms.

81. The use according to embodiment 80 in a process for heterogeneously catalyzed partial gas phase oxidation of propene to acrolein, of isobutene to methacrolein, or in a process for ammoxidation of propene to acrylonitrile or of isobutene to methacrylonitrile.

EXAMPLES AND COMPARATIVE EXAMPLES

I) Production of Annular Shaped Unsupported Catalyst Bodies B1 to B13 and of Annular Comparative Shaped Catalyst Bodies V1 to V16 with the Following Stoichiometry of the Active Material:

$[Bi_2W_4O_{15}]_p[Bi_cMo_{12}Fe_{3.0}Co_eSi_{1.6}K_{0.08}O_x]_1$.

1) Production of the Comparative Annular Shaped Unsupported Catalyst Body V1 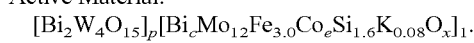
$[Bi_cMo_{12}Fe_{3.0}Co_{5.5}Si_{1.6}K_{0.08}O_x]_1$.

a) Production of the finely divided starting material A1 $Bi_2W_4O_{15}$ ($Bi_2W_2O_9\cdot2WO_3$)

In a 1.75 m³ stainless steel jacketed vessel (water for temperature control flowed through the jacket space) with a cross-beam stirrer, 214.7 kg of tungstic acid at 25° C. (74.1% by weight of W, mean particle size (according to manufacturer determined to ASTM B330) from 0.4 to 0.8 μm, ignition loss (2 h at 750° C. under air) 6-8% by weight, bulk density 5-8 g/inch³, H.C. Starck, D-38615 Goslar) were stirred (70 rpm) in portions into 773 kg of an aqueous bismuth nitrate solution in nitric acid at 25° C. (11.3% by weight of Bi; free nitric acid 3 to 5% by weight; prepared with nitric acid from bismuth metal from Sidech S.A., 1495 Tilly, Belgium, purity: >99.997% by weight of Bi, <7 mg/kg of Pb, <5 mg/kg of each of Ni, Ag, Fe, <3 mg/kg of each of Cu, Sb, and <1 mg/kg of each of Cd, Zn) at 25° C. within 20 min. The resulting aqueous mixture was then stirred at 25° C. for another 3 h and then spray-dried. The spray-drying was effected in a Niro FS 15 rotary-disk spray tower in hot air cocurrent at a gas inlet temperature of 300±10° C., a gas outlet temperature of 100±10° C., a disk speed of 18 000 rpm, a throughput of 200 l/h and an air rate of 1800 m³ (STP)/h. The resulting spray powder had an ignition loss of 12.8% by weight (calcine under air at 600° C. for 3 h in a porcelain crucible (which had been calcined to constant weight at 900° C.)) and had (at a dispersion pressure of 1.1 bar absolute) a $d_{50}$ of 28.0 μm ($d_{10}$=9.1 μm, $d_{90}$=55.2 μm). Table 1 below gives an overview of the representative $d_x$ values as a function of the absolute dispersing pressure employed:

TABLE 1

|  | 2 bar | 1.5 bar | 1.2 bar | 1.1 bar |
| --- | --- | --- | --- | --- |
| $d_{10}$ | 0.91 | 1.17 | 3.4 | 9.1 (μm) |
| $d_{50}$ | 5.8 | 8.5 | 19.7 | 28.0 (μm) |
| $d_{90}$ | 27.5 | 34.3 | 47.2 | 55.2 (μm) |

The resulting spray powder was subsequently converted to a paste with 16.7% by weight (based on the weight of the spray powder) of water at 25° C. in a discharging kneader for 30 min, and extruded by means of an extruder to extrudates of diameter 6 mm. These were cut into 6 cm sections, dried under air on a 3-zone belt dryer with a residence time of 120 min per zone at temperatures of 90-95° C. (zone 1), 115° C. (zone 2) and 125° C. (zone 3), and then treated thermally at a temperature in the region of 830° C. (calcined; in a rotary tube oven with air flew (reduced pressure 0.3 mbar, 200 m³ (STP)/h of air, 50 kg/h of extrudate, speed: 1 rpm)). What is important in the exact setting of the calcination temperature is that it has to be oriented to the desired phase composition of the calcination product, but, on the other hand, the calcined material has a BET surface area of $\geq 0.2$ m$^2$/g. The desired phases are WO$_3$ (monoclinic) and Bi$_2$W$_2$O$_9$ (orthorhombic); what is undesired here is the presence of γ-Bi$_2$WO$_6$ (russellite). Should the content of the γ-Bi$_2$WO$_6$ compound after the calcination be more than 5 intensity % (calculated as the ratio (int. r.) of the intensity of the reflection of γ-Bi$_2$WO$_6$ in the X-ray powder diffractogram at 2Θ=28.4° (CuKα radiation) to the intensity of the reflection of Bi$_2$W$_2$O$_9$ at 2Θ=30.0°), the preparation should therefore be repeated and the calcination temperature or the residence time at the same calcination temperature should be increased until the value attains or goes below the aforementioned limit. The preformed calcined mixed oxide thus obtained was ground with a 500 BQ biplex crossflow classifying mill from Hosokawa Alpine AG, Augsburg, at 2500 rpm, such that the d$_{50}$ value (measured at a dispersion pressure of 2.0 bar absolute) of the accumulated finely divided starting material A1 was d$_{50}^{A1}$=2.45 μm (d$_{10}^{A1}$=1.05 μm, d$_{90}^{A1}$=5.9 μm), the BET surface area was 0.8 m$^2$/g and the γ-Bi$_2$WO$_6$ content was 3 intensity % (=100%·in r.). The finely divided starting material A1 was then mixed in portions of 20 kg in a tilted mixer with mixing and cutting blades (mixing blade speed: 60 rpm, cutting blade speed: 3000 rpm), were mixed homogeneously with 0.5% by weight (based on the finely divided starting material A1) of Sipernat® D17:Finely divided hydrophobized SiO$_2$ from Degussa (tapped density: 150 g/l; d$_{50}$ of the SiO$_2$ particles (laser diffraction to ISO 13320-1)=10 μm, the specific surface area (nitrogen adsorption to ISO 5794-1, Annex D)=100 m$^2$/g) within 5 min.

b) Production of the Finely Divided Starting Material A2 (Mo$_{12}$Fe$_{3.0}$Co$_{5.5}$Si$_{1.6}$K$_{0.08}$)

A solution A was prepared by metering 1.075 kg of an aqueous potassium hydroxide solution (47.5% by weight KOH) at a temperature of 60° C. and subsequently, via a differential metering balance at a metering rate of 600 kg/h, 237.1 kg of ammonium heptamolybdate tetrahydrate at a temperature of 25° C. (white crystals with a particle size d of <1 mm, 81.5% by weight of MoO$_3$, 7.0-8.5% by weight of NH$_3$, max. 150 mg/kg of alkali metals, H.C. Starck, D-38642 Goslar) into 660 l of water at a temperature of 60° C. in a water-heated 1.75 m$^3$ stainless steel jacketed vessel with a crossbeam stirrer at 60° C. with stirring (70 rpm) within one minute, and the resulting slightly cloudy solution was stirred at 60° C. for 60 min (70 rpm).

A solution B was prepared by initially charging a water-heated 1.75 m$^3$ stainless steel jacketed vessel with a crossbeam stirrer at 60° C. with 282.0 kg of an aqueous cobalt(II) nitrate solution at a temperature of 60° C. (12.5% by weight of Co, prepared with nitric acid from cobalt metal from MFT Metals & Ferro-Alloys Trading GmbH, D-41747 Viersen, purity >99.6% by weight, <0.3% by weight of Ni, <100 mg/kg of Fe, <50 mg/kg of Cu), and 142.0 kg of an iron(III) nitrate nonahydrate melt at 60° C. (13.8% by weight of Fe, <0.4% by weight of alkali metals, <0.01% by weight of chloride, <0.02% by weight of sulfate, Dr. Paul Lohmann GmbH, D-81857 Emmerthal) were metered into it with stirring (70 rpm). Subsequently, the mixture was stirred for a further 30 minutes while maintaining the 60° C. Then, while maintaining the 60° C., solution B was discharged into the initially charged solution A and stirred at 70 rpm at 60° C. for a further 15 minutes. Subsequently, 19.9 kg of a Ludox TM 50 silica gel from Grace (50.1% by weight of SiO$_2$, density: 1.29 g/ml, pH 8.5 to 9.5, alkali meta, content max. 0.5% by weight)

were added to the resulting aqueous mixture which was then stirred at 70 rpm at 60° C. for a further 15 minutes.

This was followed by spray-drying in a Niro FS-15 rotary spray tower in hot air countercurrent (gas inlet temperature: 350±10° C., gas outlet temperature: 140±5° C., disk speed: 15 000 rpm, throughput: 270 kg/h, air rate 2100 m$^3$ (STP)/h). The resulting spray powder (=finely divided starting material A2) had an ignition loss of 30.0% by weight (ignite at 600° C. under air for 3 h) and a d$_{90}^{A2}$ value (measured at a dispersion pressure of 2.0 bar absolute) of 59.6 μm (d$_{10}^{A2}$=4.5 μm, d$_{50}^{A2}$=26.3 μm).

c) Production of the Comparative Annular Shaped Unsupported Catalyst Body V1

The finely divided starting material A1 comprising added Sipernat® D17 was mixed homogeneously with the finely divided starting material A2 in the amounts required for a multimetal oxide active material of the stoichiometry

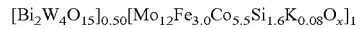

[Bi$_2$W$_4$O$_{15}$]$_{0.50}$[Mo$_{12}$Fe$_{3.0}$Co$_{5.5}$Si$_{1.6}$K$_{0.08}$O$_x$]$_1$ (total amount: 3 kg) in an Eirich intensive mixer (R02 type, capacity: 3-5 l, power: 1.9 kW, Maschinenfabrik Gustav Eirich GmbH & Co KG, D-74736 Hardheim) with bladed heads rotating counter to the plate (plate speed: 44 rpm, bladed head speed: 2500 rpm) within 5 min. Based on the aforementioned overall material, 1% by weight of TIMREX® T44 graphite from Timcal AG (d$_{50}$=20.8 μm) was additionally mixed in homogeneously at a speed of approx. 30 rpm in a drum hoop mixer (wheel diameter: 650 mm, drum volume: 5 l) within 30 minutes. The resulting mixture was then compacted in a laboratory calender with two contrarotatory steel rollers at a pressure of 9 bar and forced through a screen with a mesh size of 0.8 mm. The compactate was then mixed in the above drum hoop mixer with, based on its weight, a further 2.5% by weight of the graphite specified at a speed of approx. 30 rpm within 30 minutes, and then, as described in German application 10 2008 040 093.9, compacted in a Kilian S100 rotary tableting press (9-die tableting machine) (from Kilian, D-50735 Cologne) under a nitrogen atmosphere to give annular shaped unsupported catalyst precursor bodies (shaped bodies V) of geometry 5×3×2 mm (A (external diameter)×H (height)×I (internal diameter)) with a side crushing strength of 20±1 N and a mass of 125 mg (fill height: 7.5-9 mm, pressing force: 3.0-3.5 kN).

For the final thermal treatment, in each case 1000 g of the annular shaped unsupported catalyst precursor bodies V produced in each case, divided homogeneously between 4 grids arranged alongside one another with a square base area of in each case 150 mm×150 mm (bed height: approx. 15 mm), were heated in a forced-air oven (from Heraeus Instruments GmbH, D-63450 Hanau, type: K 750/2) through which 650 l (STP)/h of air heated to initially 140° C. flowed (instead of air, it is also possible to employ a gas stream composed of 25% by volume of N$_2$ and 75% by volume of air, or of 50% by volume of N$_2$ and 50% by volume of air, or of 75% by volume of N$_2$ and 25% by volume of air, or of 100% by volume of N$_2$) first from room temperature (25° C.) to 185° C. within 120 min. This temperature was maintained for 1 h and then increased to 225° C. within 50 min. The 225° C. was maintained for 2 h, before the temperature was increased further to 270° C. within 23 min. This temperature was likewise maintained for 1 h, before it was increased substantially linearly to 462±1° C. within 177 min. This end calcination temperature was maintained for 10 hours. This was followed by cooling to 25° C. within approx. 12 h.

The resulting annular comparative shaped unsupported catalyst body V1 had a ratio of total molar amount of bismuth present to total molar amount of molybdenum present, $n_{Bi}/n_{Mo}$, of 1/12.

2) Production of the Annular Comparative Shaped Unsupported Catalyst Body V2 ($[Bi_2W_4O_{15}]_{0.60}$ $[Mo_{12}Fe_{3.0}Co_{5.5}Si_{1.6}K_{0.08}O_x]_1$)

V2 was produced as described under 1) for V1, with the difference that, in process step 1c) the mixing ratio of starting material A1 to starting material A2 was adjusted so as to result in the stoichiometry

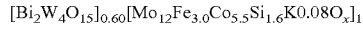

in the calcination. The $n_{Bi}/n_{Mo}$ ratio was 1.2/12.

3) Production of the Noninventive Shaped Unsupported Catalyst Body V3 ($[Bi_2W_4O_{15}]_{0.45}$ $[Mo_{12}Fe_{3.0}Co_{5.5}Si_{1.6}K_{0.08}O_x]_1$)

V3 was produced as described under 1) for V1, with the difference that, in process step 1c), the mixing ratio of starting material A1 to starting material A2 was adjusted so as to result in the stoichiometry

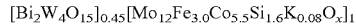

in the calcination. $n_{Bi}/n_{Mo}$ was 0.9/12.

4) Production of the Annular Comparative Shaped Unsupported Catalyst Body V4 ($[Bi_2W_4O_{15}]0.35$ $[Mo_{12}Fe_{3.0}Co_{5.5}Si_{1.6}K_{0.08}O_x]_1$)

V4 was produced as described under 1) for V1, with the difference, that in process step 1c), the mixing ratio of starting material A1 to starting material A2 was adjusted so as to result in the stoichiometry

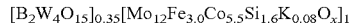

in the calcination. $n_{Bi}/n_{Mo}$ was 0.7/12.

5) Production of the Annular Comparative Shaped Unsupported Catalyst Body V5 ($[Bi_2W_4O_{15}]_{0.25}$ $[Mo_{12}Fe_{3.0}Co5.5Si_{1.6}K_{0.08}O_x]_1$)

V5 was produced as described under 1) for V1, with the difference that, in process step 1c), the mixing ratio of starting material A1 to starting material A2 was adjusted so as to result in the stoichiometry

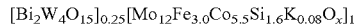

in the calcination. $n_{Bi}/n_{Mo}$ was 0.5/12.

6) Production of the Annular Shaped Unsupported Catalyst Body V6 ($[Bi_2W_4O_{15}]_{0.50}[Mo_{12}Fe_{3.0}Co_{5.5}Si_{1.6}K_{0.08}O_x]_1$)

V6 was produced as described under 1) for V1, with the difference that, in the production of the starting material A2 in process step 1b), the speed of the atomizer disk in the spray tower was increased to 18 000 rpm. The spray powder which thus resulted had an ignition loss of 30.0% by weight (calcine under air at 600° C. for 3 h) and a $d_{90}^{A2}$ value (measured at a dispersion pressure of 2.0 bar absolute) of 47.1 μm ($d_{10}^{A2}=3.9$ μm, $d_{50}^{A2}=20.3$ μm). $n_{Bi}/n_{Mo}$ was 1/12.

7) Production of the Annular Shaped Unsupported Catalyst Body V7 ($[Bi_2W_4O_{15}]_{0.50}[Mo_{12}Fe_{3.0}Co_{5.5}Si_{1.6}K_{0.08}O_x]_1$)

V7 was produced as described under 6) for V6, with the difference that, in the preparation of the starting material A1, in process step 1a), the throughput was increased so as to give rise to a $d_{50}^{A1}$ value (measured at a dispersion pressure of 2.0 bar absolute) of 3.0 μm ($d_{10}^{A1}=1.10$ μm, $d_{90}^{A1}=13.9$ μm). The BET surface area was 0.5 m²/g and the γ-$Bi_2WO_6$ content was 4 intensity %. $n_{Bi}/n_{Mo}$ was 1/12.

8) Production of the Annular Comparative Shaped Unsupported Catalyst Body V8 ($[Bi_2W_4O_{15}]_{0.50}[Mo_{12}Fe_{3.0}Co_{5.5}Si_{1.6}K_{0.08}O_x]_1$)

V8 was produced as described under 6) for V6, with the difference that, in the production of the starting material A1, in process step 1a), the throughput was reduced so as to give rise to a $d_{50}^{A1}$ value (measured at a dispersion pressure of 2.0 bar absolute) of 2.10 μm ($d_{10}^{A1}=0.92$ μm, $d_{90}^{A1}=4.7$ μm). The BET surface area was 1.2 m²/g and the γ-$Bi_2WO_6$ content was 4 intensity %. $n_{Bi}/n_{Mo}$ was 1/12.

9) Production of the Annular Comparative Shaped Unsupported Catalyst Body V9 ($[Bi_2W_4O_{15}]_{0.50}[Mo_{12}Fe_{3.0}Co_{5.5}Si_{1.6}K_{0.08}O_x]_1$)

V9 was produced as described under 6) for V6, with the difference that, in the preparation of the starting material A1, in process step 1a), the grinding in the cross flow classifying mill was followed by a further grinding in a spiral jet mill (injection pressure: 8 bar), so as to give rise to a $d_{50}^{A1}$ value (measured at a dispersion pressure of 2.0 bar absolute) of 1.60 μm ($d_{10}=0.78$ μm, $d_{90}=3.3$ μm). The BET surface area was 1.9 m²/g and the γ-$Bi_2WO_6$ content was 4 intensity %. $n_{Bi}/n_{Mo}$ was 1/12.

10) Production of the Annular Comparative Shaped Unsupported Catalyst Body V10 ($[Bi_2W_4O_{15}]_{0.50}[Mo_{12}Fe_{3.0}Co_{5.5}Si_{1.6}K_{0.08}O_x]_1$)

V10 was produced as described under 9) for V9, with the difference that, in the calcination in process step 1c), an end calcination temperature of 457±1° C. was established. $n_{Bi}/n_{Mo}$ was 1/12.

11) Production of the Annular Comparative Shaped Unsupported Catalyst Body V11 ($[Bi_2W_4O_{15}]_{0.50}[Mo_{12}Fe_{3.0}Co_{5.5}Si_{1.61}K_{0.08}O_x]_1$)

V11 was produced as described under 10) for V10, with the difference that, in the production of the starting material A2, in process step 1b), the speed of the atomizer disk in the spray tower was lowered to 12 500 rpm. The spray powder which thus resulted had an ignition loss of 30.0% by weight (calcine under air at 600° C. for 3 h) and a $d_{90}^{A2}$ value (measured at a dispersion pressure of 2.0 bar absolute) of 80.3 μm ($d_{10}^{A2}=7.0$ μm, $d_{50}^{A2}=39.4$ μm). $n_{Bi}/n_{Mo}$ was 1/12.

12) Production of the Annular Comparative Shaped Unsupported Catalyst Body V12 ($[Bi_2W_4O_{15}]_{0.10}[Mo_{12}Fe_{3.0}Co_{5.5}Si_{1.6}K_{0.08}O_x]_1$)

V12 was produced as described under 11) for V11, with the difference that, in process step 1c), the mixing ratio of starting material A1 to starting material A2 was adjusted so as to result in the stoichiometry

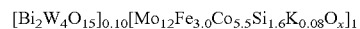

in the calcination. $n_{Bi}/n_{Mo}$ war 0.2/12.

13) Production of the Annular Comparative Shaped Unsupported Catalyst Body V13 ($[Bi_2W_4O_{15}]_{0.10}[Mo_{12}Fe_{3.0}Co_{5.5}Si_{1.6}K_{0.08}O_x]_1$)

V13 was produced as described under 12) for V12, with the difference that, in the calcination, in process step 1c), an end calcination temperature of 470±1° C. was established. $n_{Bi}/n_{Mo}$ was 0.2/12.

14) Production of the Annular Shaped Unsupported Catalyst Body V14 ($[Bi_2W_4O_{15}]_{0.50}[Mo_{12}Fe_{3.0}Co_{5.5}Si_{1.6}K_{0.08}O_x]_1$)

V14 was produced as described under 8) for V8, with the difference that, in the production of the starting material A2, in process step 1b), the speed of the atomizer disk in the spray tower was reduced to 12 500 rpm. The spray powder which thus resulted had an ignition loss of 30.0% by weight (calcine under air at 600° C. for 3 h) and a $d_{90}^{A2}$ value (measured at a dispersion pressure of 2.0 bar absolute) of 80.3 μm ($d_{10}^{A2}=7.0$ μm, $d_{50}^{A2}=39.4$ μm). $n_{Bi}/n_{Mo}$ was 1.0/12.

15) Production of the Annular Shaped Unsupported Catalyst Body V15 ($[Bi_2W_4O_{15}]_{0.50}$ $[Bi_{1.0}Mo_{12}Fe_{3.0}Co_{5.5}Si_{1.6}K0.08O_x]_1$)

V15 was produced as described under 1) for V1, with the following differences:

i) In the production of starting material A2, before the discharge of solution B into solution A with stirring (70 rpm) at 60° C., 205.7 kg of the aqueous bismuth nitrate solution in nitric acid at a temperature of 60° C. from process step 1a) were additionally metered into solution B and then stirred at 60° C. for a further 30 minutes.

ii) In the production of V15 in process step 1c), the mixing ratio of starting material A1 to starting material A2 was adjusted so as to result in the stoichiometry $$[Bi_2W_4O_{15}]_{0.50}[Bi_{1.0}Mo_{12}Fe_{3.0}Co_{5.5}Si_{1.6}K_{0.08}O_x]_1$$

in the calcination. $n_{Bi}/n_{Mo}$ was 2/12. $d_{90}^{A2}$ was 59.9 μm.

Production of the Annular Shaped Unsupported Catalyst Body V16

16) ($[Bi_{0.6}Mo_{0.2}Fe_{3.0}Co_{7.0}Si_{1.61}K_{0.08}O_x]_1$)

V16 was produced as described under 1) for V1, with the following differences:

i) In the production of solution B for starting material A2, the amount of the aqueous cobalt(II) nitrate solution was increased to 358.9 kg.

ii) In the production of starting material A2, before the discharge of solution B into solution A with stirring (70 rpm) at 60° C., 123.4 kg of the aqueous bismuth nitrate solution in nitric acid at a temperature of 60° C. from process step 1a) were additionally metered into solution B and then stirred at 60° C. for a further 30 minutes.

iii) In the production of V16, in process step 1c), the blending with starting material A1 in the Eirich intensive mixer was dispensed with. $n_{Bi}/n_{Mo}$ was thus 0.6/12. $d_{90}^{A2}$ was 59.4 μm.

17) Production of the Annular Shaped Unsupported Catalyst Body B1 ($[Bi_2W_4O_{15}]_{0.24}$ $[Bi0.02Mo_{12}Fe_{3.0}Co_{5.5}Si_{1.6}K_{0.08}O_x]_1$)

B1 was produced as described under 5) for V5, with the following differences:

i) In the production of starting material A2, before the discharge of solution B into solution A with stirring (70 rpm) at 60° C., 4.2 kg of the aqueous bismuth nitrate solution in nitric acid at a temperature of 60° C. from process step 1a) were additionally metered into solution B and then stirred at 60° C. for a further 30 minutes.

ii) In the production of B1, in process step 1c), the mixing ratio of starting material A1 to starting material A2 was adjusted so as to result in the stoichiometry $$([Bi_2W_4O_{15}]_{]0.24}[Bi_{0.02}Mo_{12}Fe_{3.0}Co_{5.5}Si_{1.6}K_{0.08}O_x]_1)$$

in the calcination. $n_{Bi}/n_{Mo}$ was 0.5/12. $d_{90}^{A2}$ was 59.5 μm.

18) Production of the Annular Shaped Unsupported Catalyst Body B2 ($[Bi_2W_4O_{15}]_{0.24}$ $[Bi_{0.02}Mo_{12}Fe_{3.0}Co_{5.5}Si_{1.6}K_{0.08}O_x]_1$)

B2 was produced as described under 17) for B1, with the difference that, in the calcination in process step 1c), an end calcination temperature of 470±1° C. was established. $n_{Bi}/n_{Mo}$ was 0.5/12.

19) Productions of the Annular Shaped Unsupported Catalyst Body B3 ($[Bi_2W_4O_{15}]_{0.235}$ $[Bi_{0.03}Mo_{12}Fe_{3.0}Co_{5.5}Si_{1.6}K_{0.08}O_x]_1$)

B3 was produced as described under 5) for V5, with the following differences:

i) In the production of starting material A2, before the discharge of solution B into solution A with stirring (70 rpm) at 60° C., 6.3 kg of the aqueous bismuth nitrate solution in nitric acid at a temperature of 60° C. from process step 1a) were additionally metered into solution B and then stirred at 60° C. for a further 30 minutes.

ii) In the production of B3 in process step 1c), the mixing ratio of starting material A1 to starting material A2 was adjusted so as to result in the stoichiometry $$[Bi_2W_4O_{15}]_{0.235}[Bi_{0.03}Mo_{12}Fe_{3.0}Co_{5.5}Si_{1.6}K_{0.08}O_x]_1$$

in the calcination. $n_{Bi}/n_{Mo}$ was 0.5/12. $d_{90}^{A2}$ was 59.6 μm.

20. Production of the Annular Shaped Unsupported Catalyst Body B4 ($[Bi_2W_4O_{15}]_{0.235}$ $[Bi_{0.03}Mo_{12}Fe_{3.0}Co_{5.5}Si_{1.6}K_{0.08}O_x]_1$)

B4 was produced as described under 19) for B3, with the difference that, in the calcination in process step 1c), an end temperature of 470±1° C. was established. $n_{Bi}/n_{Mo}$ was 0.5/12.

21. Production of the Annular Shaped Unsupported Catalyst Body B5 ($[Bi_2W_4O_{15}]_{0.345}$ $[Bi_{1.01}Mo_{12}Fe_{3.0}Co_{5.5}Si_{1.6}K_{0.08}O_x]_1$)

B5 was produced as described under 4) for V4, with the following differences:

i) In the production of starting material A2, before the discharge of solution B into solution A with stirring (70 rpm) at 60° C., 2.1 kg of the aqueous bismuth nitrate solution in nitric acid at a temperature of 60° C. from process step 1a) were additionally metered into solution B and then stirred at 60° C. for a further 30 minutes.

ii) In the production of B5 in process step 1c), the mixing ratio of starting material A1 to starting material A2 was adjusted so as to result in the stoichiometry $$[Bi_2W_4O_{15}]_{0.345}[Bi_{0.01}Mo_{12}Fe_{3.0}Co_{5.5}Si_{1.6}k_{0.08}O_x]_1$$

in the calcination. $n_{Bi}/n_{Mo}$ was 0.7/12 as for V4. $d_{90}^{A2}$ was 59.8 μm.

22. Production of the Annular Shaped Unsupported Catalyst Body B6 ($[Bi_2W_4O_{15}]_{0.34}$ $[Bi_{0.02}Mo_{12}Fe_{3.0}Co_{5.5}Si_{1.6}K_{0.08}O_x]_1$)

B6 was produced as described under 4) for V4, with the following differences:

i) In the production of starting material A2, before the discharge of solution B into solution A with stirring (70 rpm) at 60° C., 4.2 kg of the aqueous bismuth nitrate solution in nitric acid at a temperature of 60° C. from process step 1a) were additionally metered into solution B and then stirred at 60° C. for a further 30 minutes.

ii) In the production of B6 in process step 1c), the mixing ratio of starting material A1 to starting material A2 was adjusted so as to result in the stoichiometry $$[Bi_2W_4O_{15}]_{0.34}[Bi_{0.02}Mo_{12}Fe_{3.0}Co_{5.5}Si_{1.6}K_{0.08}O_x]_1$$

in the calcination. $n_{Bi}/n_{Mo}$ was 0.7/12 as for V4. $d_{90}^{A2}$ was 60.0 μm.

23. Production of the Annular Shaped Unsupported Catalyst Body B7 ($[Bi_2W_4O_{15}]_{0.325}$ $[Bi_{0.05}Mo_{12}Fe_{3.0}Co_{5.5}Si_{1.6}K_{0.08}O_x]_1$)

B7 was produced as described under 4) for V4, with the following differences:

i) In the production of starting material A2, before the discharge of solution B into solution A with stirring (70 rpm) at 60° C., 10.6 kg of the aqueous bismuth nitrate solution in nitric acid at a temperature of 60° C. from process step 1a) were additionally metered into solution B and then stirred at 60° C. for a further 30 minutes.

ii) In the production of B7 in process step 1c), the mixing ratio of starting material A1 to starting material A2 was adjusted so as to result in the stoichiometry $$[Bi_2W_4O_{15}]_{0.325}[Bi_{0.05}Mo_{12}Fe_{3.0}Co_{5.5}Si_{1.6}K_{0.08}O_x]_1$$

in the calcination. $n_{Bi}/n_{Mo}$ was 0.7/12 as for V4. $d_{90}^{A2}$ was 59.6 μm.

24. Production of the Annular Shaped Unsupported Catalyst Body B8 ($[Bi_2W_4O_{15}]_{0.30}$ $[Bi_{0.1}Mo_{12}Fe_{3.0}Co_{5.5}Si_{1.6}K_{0.08}O_x]_1$)

B8 was produced as described under 4) for V4, with the following differences:

i) In the production of starting material A2, before the discharge of solution B into solution A with stirring (70 rpm) at 60° C., 21.1 kg of the aqueous bismuth nitrate solution in nitric acid at a temperature of 60° C. from process step 1a) were additionally metered into solution B and then stirred at 60° C. for a further 30 minutes.

ii) In the production of B8 in process step 1c), the mixing ratio of starting material A1 to starting material A2 was adjusted so as to result in the stoichiometry $$[Bi_2W_4O_{15}]_{3.30}[Bi_{0.1}Mo_{12}Fe_{3.0}Co_{5.5}Si_{1.6}K_{0.080}O_x]_1$$

in the calcination. $n_{Bi}/n_{Mo}$ was 0.7/12 as for V4. $d_{90}^{A2}$ was 59.4 μm.

25. Production of the Annular Shaped Unsupported Catalyst Body B9 ($[Bi_2W_4O_{15}]_{0.30}$ $[Bi_{0.05}Mo_{12}Fe_{3.0}Co_{5.5}Si_{1.6}K_{0.08}O_x]_1$)

B9 was produced as described under 24) for B8, with the difference that, in the calcination in process step 1c), an end temperature of 457±1° C. was established. $n_{Bi}/n_{Mo}$ was 0.7/12.

26) Production of the Annular Shaped Unsupported Catalyst Body B10 ($[Bi_2W_4O_{15}]_{0.50}$ $[Bi_{0.3}Mo_{12}Fe_{3.0}Co_{5.5}Si_{1.6}K_{0.08}O_x]_1$)

B10 was produced as described under 1) for V1, with the following differences:

i) In the production of starting material A2, before the discharge of solution B into solution A with stirring (70 rpm) at 60° C., 61.7 kg of the aqueous bismuth nitrate solution in nitric acid at a temperature of 60° C. from process step 1a) were additionally metered into solution B and then stirred at 60° C. for a further 30 minutes.

ii) In the production of B10 in process step 1c), the mixing ratio of starting material A1 to starting material A2 was adjusted so as to result in the stoichiometry $$[Bi_2W_4O_{15}]_{0.50}[Bi_{0.3}Mo_{12}Fe_{3.0}Co_{5.5}Si_{1.6}K_{0.08}O_x]_1$$

in the calcination. $n_{Bi}/n_{Mo}$ was 1.3/12. $d_{90}^{A2}$ was 59.7 μm.

27) Production of the Annular Shaped Unsupported Catalyst Body B11 ($[Bi_2W_4O_{15}]_{0.50}$ $[Bi_{0.6}Mo_{12}Fe_{3.0}Co_{5.5}Si_{1.6}K_{0.08}O_x]_1$)

B11 was produced as described under 1) for V1, with the following differences:

i) In the production of starting material A2, before the discharge of solution B into solution A with stirring (70 rpm) at 60° C., 123.4 kg of the aqueous bismuth nitrate solution in nitric acid at a temperature of 60° C. from process step 1a) were additionally metered into solution B and then stirred at 60° C. for a further 30 minutes.

ii) In the production of B11, in process step 1c), the mixing ratio of starting material A1 to starting material A2 was adjusted so as to result in the stoichiometry $$[Bi_2W_4O_{15}]_{0.50}[Bi_{0.6}Mo_{12}Fe_{3.0}Co_{5.5}Si_{1.6}K_{0.08}O_x]_1$$

in the calcination. $n_{Bi}/n_{Mo}$ was 1.6/12. $d_{90}^{A2}$ was 59.9 μm.

28) Production of the Annular Shaped Unsupported Catalyst Body B12 ($[Bi_2W_4O_{15}]_{0.25}$ $[Bi_{0.6}Mo_{12}Co_{7.0}Si_{1.6}K_{0.08}O_x]_1$)

B12 was produced as described under 1) for V1, with the following differences:

i) In the production of solution B for starting material A2, the amount of the aqueous cobalt(II) nitrate solution was increased to 358.9 kg.

ii) In the production of starting material A2, before the discharge of solution B into solution A with stirring (70 rpm) at 60° C., 123.4 kg of the aqueous bismuth nitrate solution in nitric acid at a itemperature of 60° C. from process step 1a) were additionally metered into solution B and then stirred at 60° C. for a further 30 minutes.

iii) In the production of B12 in process step 1c), the mixing ratio of starting material A1 to starting material A2 was adjusted so as to result in the stoichiometry $$[Bi_2W_4O_{15}]_{0.25}[Bi_{0.6}Mo_{12}Fe_{3.0}Co_{7.0}Si_{1.6}K_{0.08}O_x]_1$$

in the calcination. $n_{Bi}/n_{Mo}$ was 1.1/12. $d_{90}^{A2}$ was 59.4 μm.

29) Production of the Annular Shaped Unsupported Catalyst Body B13 ($[Bi_2W_4O_{15}]_{0.50}$ $[Bi_{0.6}Mo_{12}Fe_{3.0}Co_{7.0}Si_{1.6}K_{0.08}O_x]_1$)

B13 was produced as described under 1) for V1, with the following differences:

i) In the production of solution B for starting material A2, the amount of the aqueous cobalt(II) nitrate solution was increased to 358.9 kg.

ii) In the production of starting material A2, before the discharge of solution B into solution A with stirring (70 rpm) at 60° C., 123.4 kg of the aqueous bismuth nitrate solution in nitric acid at a temperature of 60° C. from process step 1a) were additionally metered into solution B and then stirred at 60° C. for a further 30 minutes.

iii) In the production of B13, in process step 1c), the mixing ratio of starting material A1 to starting material A2 was adjusted so as to result in the stoichiometry $$[Bi_2W_4O_{15}]_{0.50}[Bi_{0.6}Mo_{12}Fe_{30}Co_{70}Si_{1.6}K_{0.08}O_x]_1$$

after the calcination. $n_{Bi}/n_{Mo}$ was 1.6/12. $d_{90}^{A2}$ was 59.4 μm.

II) Determination of the starting performance of the annular shaped unsupported catalyst bodies B1 to B13 and the comparative annular shaped unsupported catalyst bodies V1 to V16 in a gas phase partial oxidation of propene to acrolein catalyzed by them.

To determine the starting performance of the annular shaped unsupported catalyst bodies B1 to B13 and V1 to V16 in a gas phase partial oxidation of propene to acrolein catalyzed by them, the annular shaped unsupported catalyst bodies B1 to B13 and V1 to V16 were subjected to the test procedure described below.

A reaction tube (V2A steel; external diameter 21 mm, wall thickness 3 mm, internal diameter 15 mm, length 120 cm) was charged as follows from the top downward in the flow direction of the reaction gas mixture:

Section 1: length approx. 30 cm 40 g of steatite spheres (C220 steatite from CeramTec) with a diameter of from 1.5 to 2.0 mm as a preliminary bed (heating zone).

Section 2: length approx. 70 cm catalyst charge of 100 g of the particular annular unsupported catalyst B1 to B13 and V1 to V16

The temperature of the reaction tube was in each case controlled by means of a molecular nitrogen-sparged salt bath having the salt bath temperature $T^S$ (° C.) required in each case (53% by weight of potassium nitrate, 40% by weight of sodium nitrite and 7% by weight of sodium nitrate).

During the performance of the performance test, the reaction tube was charged continuously with a starting reaction gas mixture (charge gas mixture of air, polymer-grade propene and molecular nitrogen) of the following composition:

5% by volume of propene (polymer-grade),
9.5% by volume of oxygen, and
85.5% by volume of $N_2$.

For the purpose of determining the starting performance of the fixed catalyst bed freshly introduced into the reaction tube, a volume flow of the starting reaction gas mixture (the inlet temperature of which into the reaction tube was approx. 30° C.) of 100 l(STP)/h was fed to the reaction tube, while the salt bath temperature $T^S$ (° C.) was continuously adjusted such that the propene conversion $C^P$ (mol %) on single pass of the charge gas mixture through the reaction tube was continuously about 95 mol %. As a measure for the starting performance, after an operating time of 60 h, $T^S$ (reflects the starting activity) and the selectivity $S^{AC+AA}$ of overall target product formation (acrolein+acrylic acid) were determined in each case ($S^{AC+AA}$ in mol % of the molar amount of propene converted in single pass through the reaction tube). The pressure at the inlet into the reaction tube was 1.2 bar absolute. Tables 2 and 3 show the results determined. Furthermore, they additionally show the selectivity of acrolein formation ($S^{AC}$ (mol %)) which resulted in each case after an operating time of 60 h, and also the $d_{50}^{A1}$ (μm) and $d_{90}^{A2}$ (μm) employed in the production of the annular shaped unsupported catalyst bodies. Tables 2, 3 also show the end calcination temperatures ($T_{end\ calcination}$ (° C.)) employed in the production of the annular shaped unsupported catalyst bodies, and the stoichiometry of the particular corresponding multielement oxide I active material.

TABLE 2

| annular comparative shaped catalyst body used | $d_{50}^{A1}$/μm | $d_{90}^{A2}$/μm | $T_{end\ calcination}$/° C. | $S$/° C. | $S^{AC}$/mol % | $S^{AC+AA}$/mol % |
|---|---|---|---|---|---|---|
| 1 $[Bi_2W_4O_{15}]_{0.50}[Mo_{12}Fe_{3.0}Co_{5.5}Si_{1.6}K_{0.08}O_x]_1$ | 2.45 | 59.6 | 462 ± 1 | 31 | 86.1 | 94.3 |
| 2 $[Bi_2W_4O_{15}]_{0.60}[Mo_{12}Fe_{3.0}Co_{5.5}Si_{1.6}K_{0.08}O_x]_1$ | 2.45 | 59.6 | 462 ± 1 | 35 | 86.2 | 94.7 |
| 3 $[Bi_2W_4O_{15}]_{0.45}[Mo_{12}Fe_{3.0}Co_{5.5}Si_{1.6}K_{0.08}O_x]_1$ | 2.45 | 59.6 | 462 ± 1 | 34 | 85.1 | 93.8 |
| 4 $[Bi_2W_4O_{15}]_{0.35}[Mo_{12}Fe_{3.0}Co_{5.5}Si_{1.6}K_{0.08}O_x]_1$ | 2.45 | 59.6 | 462 ± 1 | 34 | 81.0 | 91.9 |
| 5 $[Bi_2W_4O_{15}]_{0.25}[Mo_{12}Fe_{3.0}Co_{5.5}Si_{1.6}K_{0.08}O_x]_1$ | 2.45 | 59.6 | 462 ± 1 | 35 | 75.5 | 87.7 |
| 6 $[Bi_2W_4O_{15}]_{0.50}[Mo_{12}Fe_{3.0}Co_{5.5}Si_{1.6}K_{0.08}O_x]_1$ | 2.45 | 47.1 | 462 ± 1 | 35 | 85.7 | 94.2 |
| 7 $[Bi_2W_4O_{15}]_{0.50}[Mo_{12}Fe_{3.0}Co_{5.5}Si_{1.6}K_{0.08}O_x]_1$ | 3.0 | 47.1 | 462 ± 1 | 39 | 81.6 | 91.9 |
| 8 $[Bi_2W_4O_{15}]_{0.50}[Mo_{12}Fe_{3.0}Co_{5.5}Si_{1.6}K_{0.08}O_x]_1$ | 2.10 | 47.1 | 462 ± 1 | 36 | 88.0 | 95.4 |
| 9 $[Bi_2W_4O_{15}]_{0.50}[Mo_{12}Fe_{3.0}Co_{5.5}Si_{1.6}K_{0.08}O_x]_1$ | 1.60 | 47.1 | 462 ± 1 | 48 | 88.6 | 96.4 |
| 10 $[Bi_2W_4O_{15}]_{0.50}[Mo_{12}Fe_{3.0}Co_{5.5}Si_{1.6}K_{0.08}O_x]_1$ | 1.60 | 47.1 | 457 ± 1 | 33 | 88.3 | 95.7 |
| 11 $[Bi_2W_4O_{15}]_{0.50}[Mo_{12}Fe_{3.0}Co_{5.5}Si_{1.6}K_{0.08}O_x]_1$ | 1.60 | 80.3 | 462 ± 1 | 44 | 87.1 | 95.4 |
| 12 $[Bi_2W_4O_{15}]_{0.10}[Mo_{12}Fe_{3.0}Co_{5.5}Si_{1.6}K_{0.08}O_x]_1$ | 1.60 | 80.3 | 462 ± 1 | 34 | 75.7 | 87.2 |
| 13 $[Bi_2W_4O_{15}]_{0.10}[Mo_{12}Fe_{3.0}Co_{5.5}Si_{1.6}K_{0.08}O_x]_1$ | 1.60 | 80.3 | 470 ± 1 | 30 | 86.4 | 94.3 |
| 14 $[Bi_2W_4O_{15}]_{0.50}[Mo_{12}Fe_{3.0}Co_{5.5}Si_{1.6}K_{0.08}O_x]_1$ | 2.10 | 80.3 | 462 ± 1 | 41 | 86.1 | 94.4 |
| 15 $[Bi_2W_4O_{15}]_{0.50}[Bi_{1.0}Mo_{12}Fe_{3.0}Co_{5.5}Si_{1.6}K_{0.08}O_x]_1$ | 2.45 | 59.9 | 462 ± 1 | 15 | 86.7 | 92.7 |
| 16 $Bi_{0.6}Mo_{12}Fe_{3.0}Co_{7.0}Si_{1.6}K_{0.08}O_x$ | — | 59.4 | 462 ± 1 | 06 | 90.9 | 93.3 |

TABLE 3

| Annular unsupported catalyst used | $d_{50}^{A1}$/μm | $d_{90}^{A2}$/μm | $T_{end\ calcination}$/° C. | $S$/° C. | $S^{AC}$/mol % | $S^{AC+AA}$/mol % |
|---|---|---|---|---|---|---|
| 1 $[Bi_2W_4O_{15}]_{0.24}[Bi_{0.02}Mo_{12}Fe_{3.0}Co_{5.5}Si_{1.6}K_{0.08}O_x]_1$ | 2.45 | 59.5 | 462 ± 1 | 07 | 84.5 | 91.1 |
| 2 $[Bi_2W_4O_{15}]_{0.24}[Bi_{0.02}Mo_{12}Fe_{3.0}Co_{5.5}Si_{1.6}K_{0.08}O_x]_1$ | 2.45 | 59.5 | 470 ± 1 | 18 | 88.2 | 95.1 |
| 3 $[Bi_2W_4O_{15}]_{0.235}[Bi_{0.03}Mo_{12}Fe_{3.0}Co_{5.5}Si_{1.6}K_{0.08}O_x]_1$ | 2.45 | 59.6 | 462 ± 1 | 04 | 84.5 | 91.1 |
| 4 $[Bi_2W_4O_{15}]_{0.235}[Bi_{0.03}Mo_{12}Fe_{3.0}Co_{5.5}Si_{1.6}K_{0.08}O_x]_1$ | 2.45 | 59.6 | 470 ± 1 | 21 | 89.0 | 95.0 |
| 5 $[Bi_2W_4O_{15}]_{0.345}[Bi_{0.01}Mo_{12}Fe_{3.0}Co_{5.5}Si_{1.6}K_{0.08}O_x]_1$ | 2.45 | 59.8 | 462 ± 1 | 21 | 83.7 | 92.0 |
| 6 $[Bi_2W_4O_{15}]_{0.34}[Bi_{0.02}Mo_{12}Fe_{3.0}Co_{5.5}Si_{1.6}K_{0.08}O_x]_1$ | 2.45 | 60.0 | 462 ± 1 | 18 | 87.4 | 94.2 |
| 7 $[Bi_2W_4O_{15}]_{0.325}[Bi_{0.05}Mo_{12}Fe_{3.0}Co_{5.5}Si_{1.6}K_{0.08}O_x]_1$ | 2.45 | 59.6 | 462 ± 1 | 20 | 90.6 | 96.0 |
| 8 $[Bi_2W_4O_{15}]_{0.30}[Bi_{0.1}Mo_{12}Fe_{3.0}Co_{5.5}Si_{1.6}K_{0.08}O_x]_1$ | 2.45 | 59.4 | 462 ± 1 | 29 | 91.1 | 96.6 |
| 9 $[Bi_2W_4O_{15}]_{0.30}[Bi_{0.1}Mo_{12}Fe_{3.0}Co_{5.5}Si_{1.6}K_{0.08}O_x]_1$ | 2.45 | 59.4 | 457 ± 1 | 17 | 91.2 | 96.2 |
| 10 $[Bi_2W_4O_{15}]_{0.50}[Bi_{0.3}Mo_{12}Fe_{3.0}Co_{5.5}Si_{1.6}K_{0.08}O_x]_1$ | 2.45 | 59.7 | 462 ± 1 | 28 | 91.2 | 95.8 |
| 11 $[Bi_2W_4O_{15}]_{0.50}[Bi_{0.6}Mo_{12}Fe_{3.0}Co_{5.5}Si_{1.6}K_{0.08}O_x]_1$ | 2.45 | 59.9 | 462 ± 1 | 22 | 89.5 | 94.5 |
| 12 $[Bi_2W_4O_{15}]_{0.25}[Bi_{0.6}Mo_{12}Fe_{3.0}Co_{7.0}Si_{1.6}K_{0.08}O_x]_1$ | 2.45 | 59.4 | 462 ± 1 | 05 | 91.5 | 93.9 |
| 13 $[Bi_2W_4O_{15}]_{0.50}[Bi_{0.6}Mo_{12}Fe_{3.0}Co_{7.0}Si_{1.6}K_{0.08}O_x]_1$ | 2.45 | 59.4 | 462 ± 1 | 07 | 92.1 | 94.3 |

The entirety of comparative examples V1 to V16 shows strikingly that it is impossible, in spite of extensive variations in stoichiometry, particle diameter of the starting materials A1, A2, and end calcination temperature, without bismuth doping of the T component of the multielement oxide I active material oxide, to generate a starting activity of the catalyst bed which enables a TS≦329° C. In contrast, TS in the case of all working examples B1 to B13 is homogeneously at values of ≦329° C.

A comparison of V4 with B5, B6, B7 and B8 indicates that, with identical annular shaped catalyst bodies in essentially all production aspects, those whose component T has inventive bismuth doping (as well as an increased starting activity) have an increased starting selectivity $S^{AC}$. The same applies for $S^{AC+AA}$. A comparison of V1 with B11 and B10, and of V5 with B1 and B3, likewise confirms the above finding.

V15 compared to B10 and B11 shows that, with identical annular shaped catalyst bodies in essentially all production aspects, excessively increased bismuth doping in the T component reduces the starting selectivity of target product formation ($S^{AC}$, $S^{AC+AA}$).

A comparison of B12 and B13 with V16 emphatically confirms the necessity of presence of the $[Bi_a Z^1_b O_x]_p$ component to achieve the inventive objective.

The comparison of Example B2 with B1, of Example B4 with B3, and of Example B8 with B9, indicates that a limited increase in $T_{end\ calcination}$ with otherwise essentially identical production conditions also noticeably increases $S^{AC+AA}$, but, in contrast to the inventive Bi doping, without simultaneously promoting the starting activity.

A comparison of B13 with B11 shows that an increase in the cobalt content in the T component has a positive effect on the starting activity with otherwise essentially unchanged production conditions, and promotes $S^{AC}$ relative to $S^{AA}$ (selectivity of acrylic acid formation).

U.S. Provisional Patent Application 61/096553, filed Sep. 12, 2008, is incorporated in the present application by literature reference. With regard to the abovementioned teaching, numerous changes and deviations from the present invention are possible. It can therefore be assumed that the invention, within the scope of the appended claims, can be performed differently than the way specifically described herein.

The invention claimed is:

1. A process for producing geometric shaped catalyst bodies K which comprise, as an active material, a multielement oxide I of the general stoichiometry I $$[Bi_a Z^1_b O_x]_p [Bi_c Mo_{12} Fe_d Z^2_e Z^3_f Z^4_g Z^5_h Z^6_i O_y]_1 \qquad (I),$$

where

Z¹=tungsten or tungsten and molybdenum, with the proviso that at least 10 mol % of the molar total amount of Z¹ is tungsten, Z²=one element or more than one element from the group consisting of nickel and cobalt, Z³=one element or more than one element from the group consisting of the alkali metals, the alkaline earth metals and thallium, Z⁴=one element or more than one element from the group consisting of zinc, phosphorus, arsenic, boron, antimony, tin, cerium, vanadium and chromium, Z⁵=one element or more than one element from the group consisting of silicon, aluminum, titanium, tungsten and zirconium, Z⁶=one element or more than one element from the group consisting of copper, silver, gold, yttrium, lanthanum and the lanthanides, a=0.1 to 3,
b=0.1 to 10,
d=0.01 to 5,
e=1 to 10,
f=0.01 to 2,
g=0 to 5,
h=0 to 10,
i=0 to 1,
p=0.05 to 6, and
x, y=numbers determined by the valency and frequency of the elements in I other than oxygen, in which a finely divided mixed oxide $Bi_a Z^1_b O_x$ with a particle diameter $d_{50}^{A1}$, as starting material A1, is preformed with the proviso that 1 μm≦$d_{50}^{A1}$≦100 μm;

sources of the elements other than oxygen in the component T=$[Bi_c Mo_{12} Fe_d Z^2_e Z^3_f Z^4_g Z^5_h Z^6_i O_y]_1$ of the multielement oxide I are used in an aqueous medium to obtain an intimate aqueous mixture M, with the proviso that each of the sources used, in the course of preparation of the aqueous mixture M, passes through a degree of division Q for which its diameter $d_{90}^Q$ is ≦5 μm, and the aqueous mixture M comprises the elements Bi, Mo, Fe, $Z^2$, $Z^3$, $Z^4$, $Z^5$ and $Z^6$ in the stoichiometry I*

$$Bi_c Mo_{12} Fe_d Z^2_e Z^3_f Z^4_g Z^5_h Z^6_i \qquad (I^*);$$

the aqueous mixture M, by means of drying and adjusting the degree of division $d_{90}^{A2}$, is used to obtain a finely divided starting material A2 with a particle diameter $d_{90}^{A2}$, with the proviso that 400 μm≧$d_{90}^{A2}$≧10 μm;

starting material A1 and starting material A2, or starting material A1, starting material A2 and finely divided shaping assistant, are mixed with one another to form a finely divided starting material A3, with the proviso that the starting material A3 comprises the elements other than oxygen introduced into the starting material A3 via starting materials A1 and A2 in the multielement oxide I in the stoichiometry I**

$$[Bi_a Z^1_b]_p [Bi_c Mo_{12} Fe_d Z^2_e Z^3_f Z^4_g Z^5_h Z^6_i]_1 \qquad (I^{**}),$$

finely divided starting material A3 is used to form geometric shaped bodies V, and the shaped bodies V are treated thermally at elevated temperature to obtain the geometric shaped catalyst bodies K, wherein the stoichiometric coefficient c satisfies the condition 0<c≦0.8, and wherein all particle diameters are base on volume-based particle diameter distribution determined according to ISO 13320 at a dispersion pressure of 2 bar absolute.

2. The process according to claim 1, wherein c is ≧0.001.
3. The process according to claim 1, wherein c is ≧0.002.
4. The process according to claim 1, wherein c is ≧0.005.
5. The process according to any one of claims 1 to 4, wherein c is ≦0.7.
6. The process according to any one of claims 1 to 4, wherein c is ≦0.6.
7. The process according to claim 1, wherein 0.007≦c≦0.5.
8. The process according to claim 1, wherein 0.01≦c≦0.4.
9. The process according to claim 1, wherein 0.02≦c≦0.3.
10. The process according to claim 1, wherein 0.03≦c≦0.2.
11. The process according to claim 1, wherein 0.04≦c≦0.1.
12. The process according to claim 1, wherein 0.005≦c≦0.08.
13. The process according to claim 1, wherein 0.01≦c≦0.06.
14. The process according to claim 1, wherein p is 0.1 to 4.
15. The process according to claim 1, wherein p is 0.2 to 3.
16. The process according to claim 1, wherein p is 0.3 to 1.

17. The process according to claim 1, wherein the $n_{Bi}:n_{Mo}$ ratio of the total molar amount of Bi present in the multielement oxide I, $n_{Bi}$, to the total molar amount of Mo present in the multielement oxide I, $n_{Mo}$, is 0.3 to 2:12.

18. The process according to claim 17, wherein $n_{Bi}:n_{Mo}$ is 0.4 to 1.8:12.

19. The process according to claim 17, wherein $n_{Bi}:n_{Mo}$ is 0.5 to 1.6:12.

20. The process according to claim 1, wherein $1 \text{ μm} \leq d_{50}^{A1} \leq 50 \text{ μm}$.

21. The process according to claim 1, wherein $1 \text{ μm} \leq d_{50}^{A1} \leq 10 \text{ μm}$.

22. The process according to claim 1, wherein $1.5 \text{ μm} \leq d_{50}^{A1} \leq 6 \text{ μm}$.

23. The process according to claim 1, wherein $2 \text{ μm} \leq d_{50}^{A1} \leq 3 \text{ μm}$.

24. The process according to claim 1, wherein $200 \text{ μm} \geq d_{90}^{A2} \geq 20 \text{ μm}$.

25. The process according to claim 1, wherein $150 \text{ μm} \geq d_{90}^{A2} \geq 40 \text{ μm}$.

26. The process according to claim 1, wherein $100 \text{ μm} \geq d_{90}^{A2} \geq 50 \text{ μm}$.

27. The process according to claim 1, wherein the particle diameter $d_{50}^{A2}$ of the finely divided starting material A2 satisfies the condition $10 \text{ μm} \leq d_{50}^{A2} \leq 100 \text{ μm}$.

28. The process according to claim 1, wherein the particle diameter $d_{50}^{A2}$ of the finely divided starting material A2 satisfies the condition $20 \text{ μm} \leq d_{50}^{A2} \leq 60 \text{ μm}$.

29. The process according to claim 1, wherein the ratio of the particle diameter $d_{90}^{A2}$ of the finely divided starting material A2 to the particle diameter $d_{10}^{A2}$ of the finely divided starting material A2 is in the range from 5 to 20.

30. The process according to claim 1, wherein $d_{90}^{Q}$ for each of the sources used is $\leq 3$ μm.

31. The process according to claim 1, wherein $d_{90}^{Q}$ for each of the sources used is $\leq 1$ μm.

32. The process according to claim 1, wherein $d_{90}^{Q}$ for each of the sources used is $\leq 0.5$ μm.

33. The process according to claim 1, wherein each of the sources used, in the course of preparation of the aqueous mixture M, passes through the state of a colloidal solution or of a true solution.

34. The process according to claim 1, wherein the component T comprises the element Si and each of the sources of the elements other than silicon used, in the course of preparation of the aqueous mixture M, passes through the state of a true solution and the source of the element Si used is a silica sol.

35. The process according to claim 1, wherein the finely divided starting material A2 is obtained by spray-drying the aqueous mixture M.

36. The process according to claim 1, wherein $Z^2$=Co.

37. The process according to claim 1, wherein $Z^3$=K, Cs and/or Sr.

38. The process according to claim 1, wherein $Z^5$=Si.

39. The process according to claim 1, wherein a is from 0.5 to 3.

40. The process according to claim 1, wherein a is from 1.5 to 2.5.

41. The process according to claim 1, wherein b is from 2 to 5.

42. The process according to claim 1, wherein b is from 3 to 5.

43. The process according to claim 1, wherein at least 20 mol % of the molar total amount of $Z^1$ is tungsten.

44. The process according to claim 1, wherein at least 80 mol % of the molar total amount of $Z^1$ is tungsten.

45. The process according to claim 1, wherein the molar total amount of $Z^1$ is tungsten.

46. The process according to claim 1, wherein e is from 3 to 8.

47. The process according to claim 1, wherein e is from 4 to 7.

48. The process according to claim 1, wherein f is from 0.03 to 1.

49. The process according to claim 1, wherein d is from 1 to 4.

50. The process according to claim 1, wherein h is from 0.1 to 8.

51. The process according to claim 1, wherein h is from 0.5 to 3.

52. The process according to claim 1, wherein the finely divided mixed oxide $Bi_aZ^1{}_bO_x$ is the mixed oxide $Bi_2W_4O_{15}$.

53. The process according to claim 1, wherein the product $$(d_{50}^{A1})^{0.7} \cdot (d_{90}^{A2})^{1.5} \cdot (p/2)^{-1}$$

defined as F, has a value $\geq 820$, where the two particle diameters $d_{50}^{A1}$ and $d_{90}^{A2}$ are in μm.

54. The process according to claim 53, wherein $1000 \leq F \leq 5000$.

55. The process according to claim 53, wherein $2000 \leq F \leq 4000$.

56. The process according to claim 1, wherein the product $$(d_{50}^{A1})^{0.7} \cdot (d_{90}^{A2})^{0.7} \cdot (p/2)^{-1}$$

defined as F*, has a magnitude $\geq 15$, where the two particle diameters $d_{50}^{A1}$ and $d_{90}^{A2}$ are in μm.

57. The process according to claim 56, wherein $35 \geq F^* \geq 18$.

58. The process according to claim 1, wherein finely divided starting material A1, finely divided starting material A2 and shaping assistant comprising finely divided hydrophobized silica are mixed with one another to give the finely divided starting material A3.

59. The process according to claim 1, wherein finely divided starting material A1, finely divided starting material A2 and shaping assistant comprising finely divided graphite are mixed with one another to give the finely divided starting material A3.

60. The process according to claim 1, wherein geometric shaped bodies V are formed with finely divided starting material A3 by compacting the finely divided starting material A3.

61. The process according to claim 60, wherein the compaction is effected by extrusion or tableting.

62. The process according to claim 1, wherein the geometric shaped body V is a ring.

63. The process according to claim 62, wherein the side crushing strength SCS of the annular shaped body V satisfies the condition $12 \text{ N} \leq SCS \leq 25 \text{ N}$.

64. The process according to claim 1, wherein the geometric shaped body V is a sphere.

65. The process according to claim 1, wherein the geometric shaped body V is a solid cylinder.

66. The process according to claim 62 or 63, wherein the external diameter=from 2 to 10 mm, the height=from 2 to 10 mm and the wall thickness of the ring is from 1 to 3 mm.

67. The process according to claim 64, wherein the sphere diameter is from 2 to 10 mm.

68. The process according to claim 65, wherein the external diameter=from 1 to 10 mm and the height of the solid cylinder is from 2 to 10 mm.

69. The process according to claim 1, wherein geometric shaped bodies V are formed with finely divided starting material A3 by applying the finely divided starting material A3 to the surface of a geometric shaped support body with the aid of a liquid binder.

70. The process according to claim 1, wherein the temperature of 350° C. is exceeded and the temperature of 600° C. is not exceeded in the course of thermal treatment of the shaped bodies V.

71. The process according to claim 1, wherein the temperature of 420° C. is exceeded and the temperature of 500° C. is not exceeded in the course of thermal treatment of the shaped bodies V.

72. The process according to claim 1, wherein the thermal treatment is effected in the presence of air.

73. The process according to claim 1, wherein the shaped catalyst body K is a shaped unsupported catalyst body K and the process for preparing it is followed by a process for grinding to give finely divided material and the finely divided material is applied to the surface of a geometric shaped support body with the aid of a liquid binder.

* * * * *